US012702299B2

(12) United States Patent
Hansen et al.

(10) Patent No.: US 12,702,299 B2
(45) Date of Patent: Aug. 11, 2026

(54) PERSONAL CARE SYSTEM WITH MONITOR DEVICE AND RELATED METHODS

(71) Applicant: Coloplast A/S, Humlebaek (DK)

(72) Inventors: Jais Ask Hansen, Jaegerspris (DK); Finn Speiermann, Virum (DK); Jeppe Malmberg, Copenhagen V (DK)

(73) Assignee: Coloplast A/S, Humlebaek (DK)

( * ) Notice: Subject to any disclaimer, the term of this patent is extended or adjusted under 35 U.S.C. 154(b) by 637 days.

(21) Appl. No.: 17/918,620

(22) PCT Filed: Apr. 14, 2021

(86) PCT No.: PCT/DK2021/050104

§ 371 (c)(1),
(2) Date: Oct. 13, 2022

(87) PCT Pub. No.: WO2021/209104

PCT Pub. Date: Oct. 21, 2021

(65) Prior Publication Data

US 2023/0146436 A1 May 11, 2023

(30) Foreign Application Priority Data

Apr. 14, 2020 (DK) ........................... PA 2020 70226

(51) Int. Cl.
*A61B 5/00* (2006.01)
*A61F 5/445* (2006.01)

(52) U.S. Cl.
CPC ............ *A61B 5/0022* (2013.01); *A61F 5/445* (2013.01)

(58) Field of Classification Search
CPC ....... A61B 5/0022; A61B 5/01; A61B 5/4851; A61B 5/6898; A61F 5/445; H04W 84/18
(Continued)

(56) References Cited

U.S. PATENT DOCUMENTS 2,327,514 A 8/1943 Fenwick
2,542,233 A 2/1951 Carroll
(Continued)

FOREIGN PATENT DOCUMENTS

AU 2007342523 B2 7/2011
CA 2540756 C 1/2008
(Continued)

*Primary Examiner* — Karen C Tang

(74) *Attorney, Agent, or Firm* — Coloplast Corp., Coloplast A/S; Nick Baumann

(57) ABSTRACT

Monitor device of a personal care system, devices of a personal care system, including primary accessory device and secondary accessory device, and related methods are disclosed. The monitor device comprises a processor; a memory connected to the processor; a first interface connected to the processor, the first interface configured for connecting the monitor device to the personal care appliance; and a second interface comprising a transceiver module connected to the processor and configured for connecting the monitor device to the primary accessory device and the secondary accessory device, wherein the monitor device is configured to: establish a primary connection between the monitor device and the primary accessory device; transmit primary monitor data to the primary accessory device via the primary connection; determine whether a first primary connection criterion based on a quality of the primary connection is satisfied; and in accordance with a determination that the first primary connection criterion is not satisfied, transmit secondary monitor data to the secondary accessory device.

35 Claims, 10 Drawing Sheets

(58) Field of Classification Search
USPC .......................................................... 709/224
See application file for complete search history.

(56) References Cited

U.S. PATENT DOCUMENTS 2,544,579 A 3/1951 Ardner
3,214,502 A 10/1965 Schaar
3,808,354 A 4/1974 Feezor et al.
3,832,510 A 8/1974 Pfau et al.
3,915,171 A 10/1975 Shermeta
3,941,133 A 3/1976 Chen
4,231,369 A 11/1980 Sorensen et al.
4,372,308 A 2/1983 Steer et al.
4,449,970 A 5/1984 Bevan et al.
4,668,227 A 5/1987 Kay
4,754,264 A 6/1988 Okada et al.
4,775,374 A 10/1988 Cilento et al.
4,834,731 A 5/1989 Nowak et al.
4,973,323 A 11/1990 Kaczmarek et al.
4,982,742 A 1/1991 Claude
5,013,307 A 5/1991 Broida
5,016,645 A 5/1991 Williams et al.
5,051,259 A 9/1991 Olsen et al.
5,074,851 A 12/1991 Plass et al.
5,111,812 A 5/1992 Swanson et al.
5,237,995 A 8/1993 Cano
5,318,543 A 6/1994 Ross et al.
5,358,488 A 10/1994 Suriyapa
5,486,158 A 1/1996 Samuelsen
5,519,644 A 5/1996 Benton
5,570,082 A 10/1996 Mahgerefteh et al.
5,593,397 A 1/1997 La Gro
5,626,135 A 5/1997 Sanfilippo
5,672,163 A 9/1997 Ferreira et al.
5,677,221 A 10/1997 Tseng
5,704,905 A 1/1998 Jensen et al.
5,714,225 A 2/1998 Hansen et al.
5,790,036 A 8/1998 Fisher et al.
5,800,415 A 9/1998 Olsen
5,816,252 A 10/1998 Faries et al.
5,834,009 A 11/1998 Sawers et al.
5,846,558 A 12/1998 Nielsen et al.
5,876,855 A 3/1999 Wong et al.
5,879,292 A 3/1999 Sternberg et al.
5,942,186 A 8/1999 Sanada et al.
6,015,399 A 1/2000 Mracna et al.
6,025,725 A 2/2000 Gershenfeld et al.
6,078,261 A 6/2000 Davsko
6,103,033 A 8/2000 Say et al.
6,135,986 A 10/2000 Leisner et al.
6,171,289 B1 1/2001 Millot et al.
6,206,864 B1 3/2001 Kavanagh et al.
6,241,704 B1 6/2001 Peterson et al.
6,270,445 B1 8/2001 Dean, Jr. et al.
6,407,308 B1 6/2002 Roe et al.
6,433,244 B1 8/2002 Roe et al.
6,482,491 B1 11/2002 Samuelsen et al.
6,485,476 B1 11/2002 Von et al.
6,520,943 B1 2/2003 Wagner
6,677,859 B1 1/2004 Bensen
6,764,474 B2 7/2004 Nielsen et al.
7,066,919 B1 6/2006 Sauerland et al.
7,150,728 B2 12/2006 Hansen et al.
7,166,091 B1 1/2007 Zeltner
7,199,501 B2 4/2007 Pei et al.
7,214,217 B2 5/2007 Pedersen et al.
7,326,190 B2 2/2008 Botten
7,341,578 B2 3/2008 Bulow et al.
7,347,844 B2 3/2008 Cline et al.
7,367,965 B2 5/2008 Poulsen et al.
7,559,922 B2 7/2009 Botten
7,625,362 B2 12/2009 Boehringer et al.
7,641,612 B1 1/2010 McCall
7,670,289 B1 3/2010 McCall
7,943,812 B2 5/2011 Stroebeck et al.
7,981,098 B2 7/2011 Boehringer et al.
8,061,360 B2 11/2011 Locke et al.
8,277,427 B2 10/2012 Edvardsen et al.
8,319,003 B2 11/2012 Olsen et al.
8,326,051 B1 12/2012 Hobbs
8,398,575 B1 3/2013 Mccall
8,398,603 B2 3/2013 Thirstrup et al.
8,399,732 B2 3/2013 Delund et al.
8,409,158 B2 4/2013 Edvardsen et al.
8,439,883 B1 5/2013 Johnsen
8,449,471 B2 5/2013 Tran
8,500,718 B2 8/2013 Locke et al.
8,507,081 B2 8/2013 Strobech et al.
8,632,492 B2 1/2014 Delegge
8,680,991 B2 3/2014 Tran
8,684,982 B2 4/2014 Nguyen-Demary et al.
8,740,865 B2 6/2014 Krystek et al.
8,795,257 B2 8/2014 Coulthard et al.
8,821,464 B2 9/2014 Hanuka et al.
8,975,465 B2 3/2015 Hong et al.
9,046,085 B2 6/2015 Schoess et al.
9,066,812 B2 6/2015 Edvardsen et al.
9,216,104 B2 12/2015 Thirstrup et al.
9,308,332 B2 4/2016 Heppe
9,322,797 B1 4/2016 Lastinger et al.
9,566,383 B2 2/2017 Yodfat et al.
9,629,964 B2 4/2017 Wuepper
9,675,267 B2 6/2017 Laakkonen et al.
9,693,908 B2 7/2017 Eriksson et al.
9,770,359 B2 9/2017 Edvardsen et al.
9,788,991 B2 10/2017 Bird
9,867,934 B2 1/2018 Heppe
9,928,341 B2 3/2018 Angelides
10,016,298 B2 7/2018 Thirstrup et al.
D826,740 S 8/2018 Stevens et al.
10,426,342 B2 10/2019 Hresko et al.
10,462,306 B1 * 10/2019 Siebels .................. H04W 4/24
10,500,084 B2 12/2019 Hansen et al.
10,531,977 B2 1/2020 Schoess et al.
10,646,370 B2 5/2020 Keleny et al.
10,792,184 B2 10/2020 Hvid et al.
10,799,385 B2 10/2020 Hansen et al.
10,849,781 B2 12/2020 Hansen et al.
10,874,541 B2 12/2020 Seres et al.
10,987,243 B2 4/2021 Thirstrup et al.
11,096,818 B2 8/2021 Thirstrup et al.
11,135,084 B2 10/2021 Seres et al.
11,219,436 B2 1/2022 Mayberg
11,238,133 B1 2/2022 Brewer et al.
11,306,224 B2 4/2022 Chatterjee et al.
11,314,945 B1 * 4/2022 Nguyen .................. G06F 40/42
11,406,525 B2 8/2022 Seres et al.
11,471,318 B2 10/2022 Hansen et al.
11,612,512 B2 3/2023 Hansen et al.
11,658,867 B1 * 5/2023 Kushwaha ........ H04M 15/8038
709/224
2001/0041920 A1 11/2001 Starkweather et al.
2001/0051787 A1 12/2001 Haller et al.
2002/0013613 A1 1/2002 Haller et al.
2002/0019615 A1 2/2002 Roe et al.
2002/0109621 A1 8/2002 Khair et al.
2003/0132763 A1 7/2003 Ellenz
2003/0169032 A1 9/2003 Minchole et al.
2004/0006320 A1 1/2004 Buglino et al.
2004/0030305 A1 2/2004 Sakamoto
2004/0036484 A1 2/2004 Tamai
2004/0049145 A1 3/2004 Flick
2004/0078219 A1 4/2004 Kaylor et al.
2004/0100376 A1 5/2004 Lye et al.
2004/0106908 A1 6/2004 Leise et al.
2004/0133175 A1 7/2004 Hagedorn-Olsen
2004/0171999 A1 9/2004 Andersen et al.
2004/0193122 A1 9/2004 Cline et al.
2004/0193123 A1 9/2004 Fenton
2004/0216833 A1 11/2004 Fleming et al.
2005/0054997 A1 3/2005 Buglino et al.
2005/0065488 A1 3/2005 Elliott
2005/0070863 A1 3/2005 Bulow et al.
2005/0085779 A1 4/2005 Poulsen et al.

(56) References Cited

U.S. PATENT DOCUMENTS

2005/0101841 A9 5/2005 Kaylor et al.
2005/0113704 A1 5/2005 Lawson et al.
2005/0240163 A1 10/2005 Andersen
2005/0256545 A1 11/2005 Koh et al.
2005/0261645 A1 11/2005 Conrad et al.
2006/0015081 A1 1/2006 Suzuki et al.
2006/0025727 A1 2/2006 Boehringer et al.
2006/0052752 A1 3/2006 McMichael
2006/0194324 A1 8/2006 Faries et al.
2006/0271002 A1 11/2006 Botten
2007/0010256 A1 1/2007 Klabunde et al.
2007/0035405 A1 2/2007 Wada et al.
2007/0135782 A1 6/2007 Bager et al.
2007/0185464 A1 8/2007 Fattman et al.
2007/0203407 A1 8/2007 Hoss et al.
2007/0204691 A1 9/2007 Bogner et al.
2008/0038536 A1 2/2008 Strobech et al.
2008/0041792 A1 2/2008 Crnkovich et al.
2008/0071214 A1 3/2008 Locke et al.
2008/0075934 A1 3/2008 Barlow et al.
2008/0091154 A1 4/2008 Botten
2008/0140057 A1 6/2008 Wood et al.
2008/0234641 A1 9/2008 Locke et al.
2008/0255808 A1 10/2008 Hayter
2008/0275327 A1 11/2008 Faarbaek et al.
2008/0278337 A1 11/2008 Huang et al.
2008/0300559 A1 12/2008 Gustafson et al.
2008/0300578 A1 12/2008 Freedman
2008/0306459 A1 12/2008 Albrectsen
2009/0012501 A1 1/2009 Boehringer et al.
2009/0118687 A1 5/2009 Kristensen et al.
2009/0167286 A1 7/2009 Naylor et al.
2009/0173935 A1 7/2009 Cho et al.
2009/0227969 A1 9/2009 Jaeb et al.
2009/0234916 A1 9/2009 Cosentino et al.
2009/0247970 A1 10/2009 Keleny et al.
2009/0264957 A1 10/2009 Giftakis et al.
2010/0010460 A1 1/2010 Butler
2010/0030167 A1 2/2010 Thirstrup et al.
2010/0072271 A1 3/2010 Thorstensson
2010/0106220 A1 4/2010 Ecker et al.
2010/0114047 A1 5/2010 Song et al.
2010/0271212 A1 10/2010 Page
2010/0311167 A1 12/2010 Wood et al.
2011/0034890 A1 2/2011 Stroebech et al.
2011/0077497 A1 3/2011 Oster et al.
2011/0130642 A1 6/2011 Jaeb et al.
2011/0144470 A1 6/2011 Mazar et al.
2011/0191044 A1 8/2011 Stafford
2011/0245682 A1 10/2011 Robinson et al.
2011/0246983 A1 10/2011 Brunet et al.
2011/0257496 A1 10/2011 Terashima et al.
2012/0013130 A1 1/2012 Jung
2012/0089037 A1 4/2012 Bishay et al.
2012/0143154 A1 6/2012 Edvardsen et al.
2012/0143155 A1 6/2012 Edvardsen et al.
2012/0258302 A1 10/2012 Hunt et al.
2012/0283678 A1 11/2012 Nguyen-Demary et al.
2012/0304767 A1 12/2012 Howard et al.
2012/0323086 A1 12/2012 Hansen
2013/0018231 A1 1/2013 Hong et al.
2013/0030167 A1 1/2013 Wang et al.
2013/0030397 A1 1/2013 Sabeti
2013/0060213 A1 3/2013 Hanuka et al.
2013/0066285 A1 3/2013 Locke et al.
2013/0072886 A1 3/2013 Schertiger et al.
2013/0078912 A1 3/2013 San Vicente et al.
2013/0086217 A1 4/2013 Price et al.
2013/0102979 A1 4/2013 Coulthard et al.
2013/0138065 A1 5/2013 Buus
2013/0150769 A1 6/2013 Heppe
2013/0165862 A1 6/2013 Griffith et al.
2013/0192604 A1 8/2013 Persson et al.
2013/0226116 A1 8/2013 Edvardsen et al.
2013/0231620 A1 9/2013 Thirstrup et al.
2013/0254141 A1 9/2013 Barda et al.
2013/0303867 A1 11/2013 Elfstrom et al.
2013/0307570 A1 11/2013 Bosaeus et al.
2013/0324952 A1 12/2013 Krystek et al.
2013/0324955 A1 12/2013 Wong et al.
2013/0332085 A1 12/2013 Yang et al.
2014/0051946 A1 2/2014 Arne et al.
2014/0128815 A1 5/2014 Cabiri et al.
2014/0200426 A1 7/2014 Taub et al.
2014/0200538 A1 7/2014 Euliano et al.
2014/0236111 A1 8/2014 Casado et al.
2014/0275854 A1 9/2014 Venkatraman et al.
2014/0276501 A1 9/2014 Cisko
2014/0288381 A1 9/2014 Faarbaek et al.
2014/0309600 A1 10/2014 Aceto et al.
2014/0323909 A1 10/2014 Kim
2014/0327433 A1 11/2014 Anway et al.
2014/0336493 A1 11/2014 Kulach et al.
2015/0057634 A1 2/2015 Mastrototaro et al.
2015/0150457 A1 6/2015 Wu et al.
2015/0151051 A1 6/2015 Tsoukalis
2015/0230706 A1 8/2015 Nakagawa et al.
2015/0231802 A1 8/2015 Quan et al.
2015/0250639 A1 9/2015 Thirstrup et al.
2015/0257923 A1 9/2015 Thirstrup et al.
2015/0328389 A1 11/2015 Heppe
2015/0342777 A1 12/2015 Seres et al.
2015/0374896 A1 12/2015 Du et al.
2016/0008182 A1 1/2016 Prokopuk et al.
2016/0058604 A1 3/2016 Wiltshire et al.
2016/0084869 A1 3/2016 Yuen et al.
2016/0103966 A1 4/2016 Mirza
2016/0117062 A1 4/2016 Hussam et al.
2016/0158056 A1 6/2016 Davis et al.
2016/0158517 A1 6/2016 Nebbia
2016/0158969 A1 6/2016 Mclane et al.
2016/0166438 A1 6/2016 Rovaniemi
2016/0178387 A1 6/2016 Yamasaki et al.
2016/0198996 A1 7/2016 Dullen
2016/0218555 A1 7/2016 Slaby et al.
2016/0235581 A1 8/2016 Keleny et al.
2016/0235582 A1 8/2016 Moavenian
2016/0242654 A1 8/2016 Quinlan et al.
2016/0278990 A1 9/2016 Chen
2016/0305776 A1 10/2016 Mrtensson et al.
2016/0310077 A1 10/2016 Hunter et al.
2016/0310140 A1 10/2016 Belson et al.
2016/0310329 A1 10/2016 Patel et al.
2016/0331232 A1 11/2016 Love et al.
2016/0331235 A1 11/2016 Nyberg et al.
2016/0361015 A1 12/2016 Wang et al.
2017/0042614 A1 2/2017 Salahieh et al.
2017/0050004 A1 2/2017 Tilson et al.
2017/0055896 A1 3/2017 Al-Ali et al.
2017/0090236 A1 3/2017 Yeh et al.
2017/0098044 A1 4/2017 Lai et al.
2017/0113001 A1 4/2017 Trock
2017/0140103 A1 5/2017 Angelides
2017/0156920 A1 6/2017 Hunt et al.
2017/0181628 A1 6/2017 Burnette et al.
2017/0340474 A1 11/2017 Thirstrup et al.
2017/0340498 A1 11/2017 Tessmer et al.
2017/0348137 A1 12/2017 Hvid et al.
2017/0348162 A1 12/2017 Arizti et al.
2017/0360592 A1 12/2017 Carrubba
2017/0360593 A1 12/2017 Cox
2018/0049667 A1 2/2018 Heppe
2018/0055359 A1 3/2018 Shamim et al.
2018/0109852 A1 4/2018 Mandapaka et al.
2018/0110078 A1 4/2018 Mandapaka et al.
2018/0136712 A1 5/2018 Niikura et al.
2018/0171183 A1 6/2018 Sakurai et al.
2018/0298240 A1 10/2018 Chatterjee et al.
2018/0318475 A1 11/2018 Thomson et al.
2019/0008439 A1 1/2019 Sageder et al.
2019/0133810 A1 5/2019 Seres et al.
2019/0133811 A1 5/2019 Seres et al.
2019/0133812 A1 5/2019 Seres et al.
2019/0142623 A1 5/2019 Schoess et al.

(56) References Cited

U.S. PATENT DOCUMENTS

2019/0175386 A1 6/2019 Monty
2019/0182838 A1* 6/2019 Bondarenko ..... H04M 15/7652
2019/0184093 A1 6/2019 Sjolund et al.
2019/0192066 A1 6/2019 Schoess et al.
2019/0192332 A1 6/2019 Hansen et al.
2019/0192333 A1 6/2019 Hansen et al.
2019/0192334 A1 6/2019 Hansen et al.
2019/0240059 A1 8/2019 Seres et al.
2019/0247050 A1 8/2019 Goldsmith
2019/0297487 A1* 9/2019 Muñoz Sanchez ... H04L 67/535
2019/0307405 A1* 10/2019 Terry ..................... G16H 10/60
2019/0374163 A1 12/2019 Faarbaek et al.
2020/0100931 A1 4/2020 Schoess et al.
2020/0188161 A1 6/2020 Seres et al.
2020/0214054 A1* 7/2020 Qiao ................. H04M 15/8228
2020/0246174 A1 8/2020 Hansen et al.
2020/0246175 A1 8/2020 Hansen et al.
2020/0246176 A1 8/2020 Hansen et al.
2020/0246177 A1 8/2020 Hansen et al.
2020/0276063 A1 9/2020 Muñoz Herencia
2020/0279368 A1 9/2020 Tada et al.
2020/0296177 A1* 9/2020 Hammer ............ G06Q 30/0202
2020/0297244 A1 9/2020 Brownhill et al.
2020/0306074 A1 10/2020 Speiermann et al.
2020/0322793 A1 10/2020 Yang
2020/0330258 A1 10/2020 Hansen et al.
2020/0330260 A1 10/2020 Hansen et al.
2020/0337880 A1 10/2020 Hansen et al.
2020/0337881 A1 10/2020 Hansen et al.
2020/0337882 A1 10/2020 Hansen et al.
2020/0337883 A1 10/2020 Hansen et al.
2020/0351626 A1* 11/2020 Libby .................. H04M 15/64
2020/0375499 A1 12/2020 Hansen et al.
2020/0375782 A1 12/2020 Hansen et al.
2020/0375783 A1 12/2020 Hansen et al.
2020/0375784 A1 12/2020 Hansen et al.
2020/0375785 A1 12/2020 Hansen et al.
2020/0375786 A1 12/2020 Hansen et al.
2020/0375809 A1 12/2020 Sullivan et al.
2020/0383637 A1 12/2020 Hansen et al.
2020/0383818 A1 12/2020 Hansen et al.
2020/0383819 A1 12/2020 Sletten et al.
2020/0383820 A1 12/2020 Hansen et al.
2020/0383821 A1 12/2020 Hansen et al.
2020/0389331 A1* 12/2020 Karri ..................... H04L 47/781
2020/0390587 A1 12/2020 Svanegaard et al.
2020/0390588 A1 12/2020 Hansen et al.
2020/0390589 A1 12/2020 Hansen et al.
2020/0395120 A1 12/2020 Svanegaard et al.
2020/0395610 A1 12/2020 Ono et al.
2020/0405228 A1 12/2020 Svanegaard et al.
2020/0405229 A1 12/2020 Svanegaard et al.
2020/0405230 A1 12/2020 Svanegaard et al.
2021/0000414 A1 1/2021 Svanegaard et al.
2021/0000633 A1 1/2021 Hansen et al.
2021/0000634 A1 1/2021 Svanegaard et al.
2021/0000635 A1 1/2021 Hansen et al.
2021/0000636 A1 1/2021 Hansen et al.
2021/0007663 A1 1/2021 Svanegaard et al.
2021/0007881 A1 1/2021 Svanegaard et al.
2021/0015653 A1 1/2021 Hansen et al.
2021/0015654 A1 1/2021 Hansen et al.
2021/0022683 A1 1/2021 Faarbaek et al.
2021/0038424 A1 2/2021 Svanegaard et al.
2021/0059603 A1 3/2021 Svanegaard et al.
2021/0085511 A1 3/2021 Hansen et al.
2021/0085512 A1 3/2021 Hansen et al.
2021/0100533 A1 4/2021 Seres et al.
2021/0122261 A1* 4/2021 Qiao ....................... H04W 4/40
2021/0127303 A1* 4/2021 Yoon ..................... H04W 24/08
2021/0128364 A1 5/2021 Cole et al.
2021/0177642 A1 6/2021 Andersen et al.
2021/0194709 A1* 6/2021 Yadav ................. H04M 15/735
2021/0195732 A1* 6/2021 Longinotti-Buitoni ...................... H05K 3/361
2021/0212855 A1 7/2021 Hansen et al.
2021/0228194 A1 7/2021 Mayberg
2021/0338471 A1 11/2021 Nolan et al.
2021/0361464 A1 11/2021 Larsen et al.
2021/0361465 A1 11/2021 Hansen et al.
2021/0361466 A1 11/2021 Hansen et al.
2021/0361467 A1 11/2021 Hansen et al.
2021/0369197 A1 12/2021 Hansen et al.
2021/0369488 A1 12/2021 Hansen et al.
2021/0369489 A1 12/2021 Hansen et al.
2021/0369490 A1 12/2021 Hansen et al.
2021/0370217 A1 12/2021 Kirschman
2021/0386368 A1 12/2021 Carlsson et al.
2021/0397435 A1 12/2021 Le et al.
2022/0000652 A1 1/2022 Thirstrup et al.
2022/0031227 A1 2/2022 Cho et al.
2022/0031495 A1 2/2022 Seres et al.
2022/0079802 A1 3/2022 Hansen
2022/0079803 A1 3/2022 Windeballe et al.
2022/0087851 A1 3/2022 Stroebech
2022/0104005 A1* 3/2022 Xiong .................. H04W 12/45
2022/0110585 A1 4/2022 Andersen
2022/0117771 A1 4/2022 Fearn et al.
2022/0142807 A1 5/2022 Tofte
2022/0167176 A1* 5/2022 Khalid .............. H04W 72/1215
2022/0192860 A1 6/2022 Hansen et al.
2022/0241104 A1 8/2022 Knoedler
2022/0241105 A1 8/2022 Hansen et al.
2022/0265458 A1 8/2022 Carlsson et al.
2022/0286822 A1* 9/2022 Saxena ................ H04M 15/66
2022/0322202 A1* 10/2022 Li ......................... H04M 15/93
2023/0027934 A1* 1/2023 Raleigh ............... H04L 12/1407
2023/0029236 A1* 1/2023 Qiao ..................... H04M 15/61
2023/0059470 A1 2/2023 Hansen et al.
2023/0064734 A1 3/2023 Hansen et al.
2023/0105402 A1 4/2023 Hansen et al.
2023/0117727 A1 4/2023 Hansen et al.
2023/0118594 A1 4/2023 Speiermann et al.
2023/0141297 A1 5/2023 Herold et al.
2023/0145670 A1 5/2023 Seres et al.
2023/0190509 A1 6/2023 Hansen et al.
2023/0210682 A1 7/2023 Hansen et al.
2023/0233147 A1 7/2023 Hansen et al.
2023/0329893 A1 10/2023 Olsen et al.
2023/0338005 A1 10/2023 Barthe et al.

FOREIGN PATENT DOCUMENTS

CA 3009449 C 9/2019
CA 3002372 C 3/2021
CA 2947016 C 2/2023
CN 103269668 A 8/2013
CN 203786580 U 8/2014
CN 104902399 A 9/2015
CN 104980878 A 10/2015
CN 105588856 A 5/2016
CN 206271160 U 6/2017
CN 206450708 U 8/2017
CN 105615896 B 5/2019
CN 105359167 B 6/2019
DE 3437950 A1 4/1985
DE 3836590 A1 5/1990
DE 19953062 A1 5/2000
DE 19900611 C1 7/2000
DE 102011014321 A1 9/2012
DE 102011076219 A1 11/2012
EP 0168967 A1 1/1986
EP 0373782 A1 6/1990
EP 0416397 A1 3/1991
EP 0850076 B1 4/2005
EP 1188157 B1 12/2005
EP 2108345 A1 10/2009
EP 2489561 A2 8/2012
EP 2654646 A2 10/2013
EP 2738960 A1 6/2014
EP 2453851 B1 10/2014
EP 3064179 A1 9/2016
EP 3213727 A1 9/2017
GB 2219679 A 12/1989

(56) References Cited

FOREIGN PATENT DOCUMENTS

| | | | |
|---|---|---|---|
| GB | 2225951 | A | 6/1990 |
| GB | 2343628 | A | 5/2000 |
| GB | 2465742 | A | 6/2010 |
| GB | 2542093 | A | 3/2017 |
| GB | 2561193 | A | 10/2018 |
| JP | 04-074882 | A | 3/1992 |
| JP | 06-152077 | A | 5/1994 |
| JP | 09-010184 | A | 1/1997 |
| JP | 11-128352 | A | 5/1999 |
| JP | 2000-093448 | A | 4/2000 |
| JP | 2001-087299 | A | 4/2001 |
| JP | 2002-055074 | A | 2/2002 |
| JP | 2002-224093 | A | 8/2002 |
| JP | 2005-323981 | A | 11/2005 |
| JP | 2007-319561 | A | 12/2007 |
| JP | 2014-033745 | A | 2/2014 |
| JP | 2014-054368 | A | 3/2014 |
| JP | 2014-507182 | A | 3/2014 |
| KR | 10-2012-0003987 | A | 1/2012 |
| NL | 1003904 | C2 | 3/1998 |
| RU | 2527155 | C2 | 8/2014 |
| TW | 201201783 | A | 1/2012 |
| WO | 94/15562 | A1 | 7/1994 |
| WO | 97/10012 | A1 | 3/1997 |
| WO | 99/33037 | A1 | 7/1999 |
| WO | 99/36017 | A1 | 7/1999 |
| WO | 00/79497 | A1 | 12/2000 |
| WO | 01/13830 | A1 | 3/2001 |
| WO | 01/50996 | A1 | 7/2001 |
| WO | 02/52302 | A2 | 7/2002 |
| WO | 02/99765 | A1 | 12/2002 |
| WO | 2005/038693 | A1 | 4/2005 |
| WO | 2005/082271 | A2 | 9/2005 |
| WO | 2006/008866 | A1 | 1/2006 |
| WO | 2006/094513 | A2 | 9/2006 |
| WO | 2007/000168 | A1 | 1/2007 |
| WO | 2007/059774 | A2 | 5/2007 |
| WO | 2007/070266 | A1 | 6/2007 |
| WO | 2007/098762 | A1 | 9/2007 |
| WO | 2007/133555 | A2 | 11/2007 |
| WO | 2007128038 | A1 | 11/2007 |
| WO | 2008/057884 | A2 | 5/2008 |
| WO | 2009/006900 | A1 | 1/2009 |
| WO | 2009/052496 | A1 | 4/2009 |
| WO | 2009/107011 | A1 | 9/2009 |
| WO | 2009/112912 | A2 | 9/2009 |
| WO | 2011/003421 | A1 | 1/2011 |
| WO | 2011/004165 | A1 | 1/2011 |
| WO | 2011/061540 | A1 | 5/2011 |
| WO | 2011/105701 | A2 | 9/2011 |
| WO | 2011/123018 | A1 | 10/2011 |
| WO | 2011/139499 | A1 | 11/2011 |
| WO | 2011/161254 | A2 | 12/2011 |
| WO | 2012/068386 | A1 | 5/2012 |
| WO | 2012/076022 | A2 | 6/2012 |
| WO | 2012/084987 | A2 | 6/2012 |
| WO | 2013/013197 | A1 | 1/2013 |
| WO | 2013095231 | A1 | 6/2013 |
| WO | 2014/004207 | A1 | 1/2014 |
| WO | 2014/086369 | A1 | 6/2014 |
| WO | 2015/007284 | A1 | 1/2015 |
| WO | 2015/014774 | A1 | 2/2015 |
| WO | 2015/084462 | A1 | 6/2015 |
| WO | 2015/094064 | A1 | 6/2015 |
| WO | 2015/187366 | A1 | 12/2015 |
| WO | 2016/132738 | A1 | 8/2016 |
| WO | 2016/166731 | A1 | 10/2016 |
| WO | 2016162038 | A1 | 10/2016 |
| WO | 2016/192738 | A1 | 12/2016 |
| WO | 2017/023794 | A1 | 2/2017 |
| WO | 2017/062042 | A1 | 4/2017 |
| WO | 2017/067558 | A1 | 4/2017 |
| WO | 2017/067560 | A1 | 4/2017 |
| WO | 2017/074505 | A1 | 5/2017 |
| WO | 2017/088153 | A1 | 6/2017 |
| WO | 2017108109 | A1 | 6/2017 |
| WO | 2017/136696 | A1 | 8/2017 |
| WO | 2017/190752 | A1 | 11/2017 |
| WO | 2018/028756 | A1 | 2/2018 |
| WO | 2019/094635 | A1 | 5/2019 |
| WO | 2019/120432 | A1 | 6/2019 |
| WO | 2019/161859 | A1 | 8/2019 |
| WO | 2019/161860 | A1 | 8/2019 |
| WO | 2019/161863 | A1 | 8/2019 |
| WO | 2019/174693 | A1 | 9/2019 |
| WO | 2019/174695 | A1 | 9/2019 |
| WO | 2019174694 | A1 | 9/2019 |
| WO | 2019/213623 | A1 | 11/2019 |
| WO | WO-2019226273 | A1 * | 11/2019 ........... A61B 5/0008 |
| WO | 2020/035121 | A1 | 2/2020 |

* cited by examiner

PERSONAL CARE SYSTEM WITH MONITOR DEVICE AND RELATED METHODS

The present disclosure relates to a personal care system, devices thereof and related methods. The personal care system comprises a personal care appliance, such as an ostomy appliance or a wound dressing, a monitor device, and a plurality of accessory devices including a primary accessory device and a secondary accessory device. In particular, the present disclosure relates to operation of a monitor device and accessory device in scenarios where one or more connections are lost or degraded.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
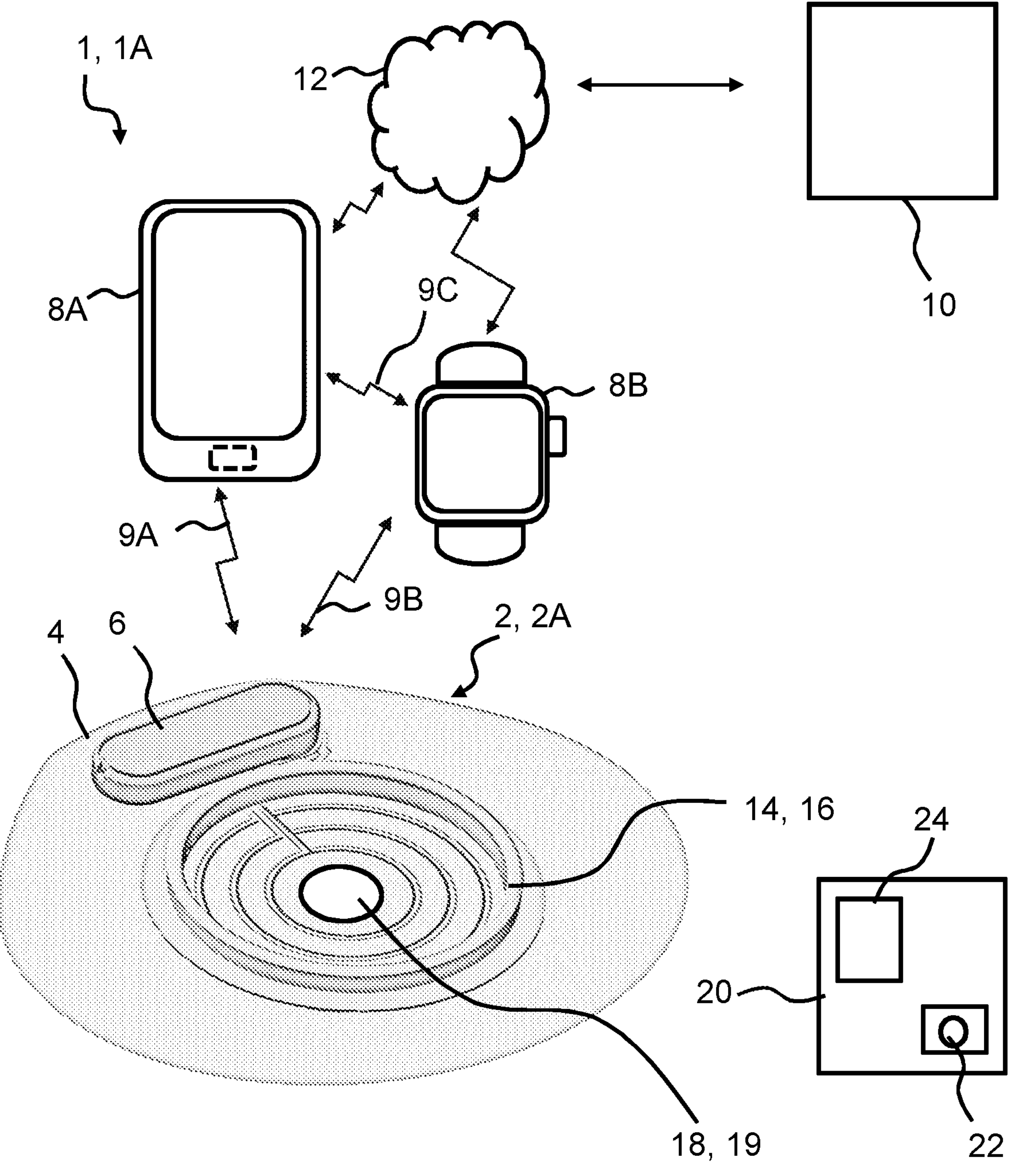
FIG. 1 illustrates an exemplary personal care system being an ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance/wound dressing appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance or wound dressing than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to a personal care system and devices thereof, such as a personal care appliance, an electrode assembly, a monitor device, and optionally one or more accessory devices, such as a primary accessory device and/or a secondary accessory device. Further, methods related to the personal care system and devices thereof are disclosed. An accessory device (also referred to as an external device), such as the primary accessory device and/or the secondary accessory device, may be a mobile phone or other handheld device, such as a tablet computer. An accessory device, such as the primary accessory device and/or the secondary accessory device, may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The personal care system may comprise a server device. The server device may be operated and/or controlled by the personal care appliance manufacturer and/or a service centre. The monitor device and/or the primary accessory device are configured to establish a primary connection therebetween. The primary connection may be a Bluetooth connection or other wireless connection. The monitor device and/or the secondary accessory device are configured to establish a secondary connection therebetween. The secondary connection may be a Bluetooth connection or other wireless connection. The primary accessory device and/or the secondary accessory device are optionally configured to establish an accessory connection therebetween. The accessory connection may be a Bluetooth connection or other wireless connection.

The present disclosure provides a personal care system and devices thereof, such as a personal care appliance, e.g. an ostomy appliance or a wound dressing, a monitor device, and optionally one or more accessory devices which either alone or together facilitate reliable determination and monitoring of the nature, severity and rapidness of moisture propagation in the personal appliance, such as in an adhesive material provided for attaching a base plate of an ostomy appliance to the skin surface of a user or in an absorbent core of the wound dressing.

The personal care system may be an ostomy system. Thus, the personal care appliance may be an ostomy appliance.

The personal care system may be a wound dressing system. Thus, the personal care appliance may be a wound dressing appliance also denoted wound dressing. A wound dressing system and devices thereof are provided, such as a wound dressing, a monitor device, and optionally one or more accessory devices which either alone or together facilitate reliable monitoring of the wound dressing and operating state thereof. Accordingly, the wound dressing system and devices thereof enable providing information to the user about the operating state of the wound dressing, and in turn optionally enable providing an indication to the user or a caretaker of the remaining time frame for replacing the wound dressing without experiencing leakage and/or to provide optimum wound healing conditions.

The personal care system may be a catheter system. Thus, the personal care appliance may be a catheter appliance.

The personal care system comprises one or more of a personal care appliance, a monitor, a primary accessory device, and a secondary accessory device as described herein.

Depending on the nature of the pattern of moisture propagation in the personal care appliance, the personal care system and devices thereof enable providing information to the user about the status and/or a type of failure, and in turn enable providing an indication to the user of the severity and thus the remaining time frame for replacing the personal care appliance without experiencing severe leakage and/or skin damage and/or to improve wound healing.

In particular, the present disclosure ensures or facilitates that essential data related to the monitoring of the personal care appliance are not lost or at least maintained in the system during connection loss. Further, the present disclosure provides that information to the user about the status and/or a type of failure in the personal care appliance is provided even in case of connection loss in the system. The present disclosure allows higher flexibility to a user, e.g. in scenarios where the user does not have access to the primary accessory device, e.g. during work-out, shopping, work, etc.

It is as important aspect of the present disclosure that a personal care system with redundancy in accessory device functionality is provided.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area. The ostomy appliance may comprise an electrode assembly or the ostomy system optionally comprises an electrode assembly mountable on a proximal side of the base plate of the ostomy appliance. The electrode assembly, also denoted sensor assembly or sensor patch, comprises a plurality of electrodes optionally arranged on a distal side of a first adhesive layer of the ostomy appliance or on a distal side of a first adhesive layer of the electrode assembly, the plurality of electrodes forming a plurality of sensors (electrode pairs). The ostomy appliance/electrode assembly may comprise a monitor interface for connecting electrodes of the electrode assembly to terminals of the first interface of the monitor device.

The wound dressing appliance comprises a top layer, a first adhesive layer with a proximal surface configured for attachment of the wound dressing to the skin surface of a user; an absorbent core layer; and an electrode assembly comprising a plurality of electrodes optionally arranged on a distal side of the absorbent core layer, the plurality of electrodes forming a plurality of sensors (electrode pairs). The top layer is optionally on a distal side of the electrode assembly. The wound dressing may comprise a monitor interface for connecting electrodes of the electrode assembly to terminals of the first interface of the monitor device.

A monitor device for a personal care system is disclosed, the personal care system comprising a personal care appliance, the monitor device, a primary accessory device, and a secondary accessory device, the monitor device comprising a processor; a memory connected to the processor; a first interface connected to the processor, the first interface configured for connecting the monitor device to the personal care appliance; and a second interface comprising a transceiver module connected to the processor and configured for connecting the monitor device to the primary accessory device and/or the secondary accessory device. The monitor device is configured to establish a primary connection between the monitor device and the primary accessory device; transmit primary monitor data to the primary accessory device via the primary connection; determine whether a first primary connection criterion based on a quality of the primary connection is satisfied; and in accordance with a determination that the first primary connection criterion is not satisfied, transmit secondary monitor data, e.g. to the secondary accessory device.

Monitor data, such as the primary monitor data and/or the secondary monitor data, may comprise appliance data (also denoted a first part of monitor data) optionally indicative of a physical condition of the personal care appliance. The appliance data may be ostomy data indicative of a physical condition of the ostomy appliance, such as a physical condition of a base plate of the ostomy appliance and/or electrode assembly. The appliance data may be wound dressing data indicative of a physical condition of the wound dressing appliance, such as a physical condition of an absorbent core layer and/or electrode assembly of the wound dressing appliance. Accordingly, the primary monitor data may comprise primary appliance data and/or the secondary monitor data may comprise secondary appliance data.

The appliance data, such as the primary appliance data and/or the secondary appliance data, may comprise first appliance sensor data obtained from or derived from a first sensor (first electrode pair) of the personal care appliance. The first sensor may be an outer or outermost sensor of an ostomy appliance/electrode assembly. The first sensor may be a sensor arranged at or near a periphery of an absorbent core of a wound dressing appliance. The appliance data, such as the primary appliance data and/or the secondary appliance data, may comprise second appliance sensor data obtained from or derived from a second sensor (second electrode pair) of the personal care appliance. The second sensor may be an inner or innermost sensor of an ostomy appliance/electrode assembly. The second sensor may be a sensor centrally located on an absorbent core of a wound dressing appliance. The appliance data, such as the primary appliance data and/or the secondary appliance data, may comprise third appliance sensor data obtained from or derived from a third sensor (third electrode pair) of the personal care appliance. The third sensor may be an inner or innermost sensor of an ostomy appliance/electrode assembly. The appliance data, such as the primary appliance data and/or the secondary appliance data, may comprise fourth appliance sensor data obtained from or derived from a fourth sensor (fourth electrode pair) of the personal care appliance. The fourth sensor may be an inner or innermost sensor of an ostomy appliance/electrode assembly. The appliance data, such as the primary appliance data and/or the secondary appliance data, may comprise fifth appliance sensor data obtained from or derived from a fifth sensor (fifth electrode pair) of the personal care appliance. The fifth sensor may be a sensor of an ostomy appliance/electrode assembly arranged between an inner sensor and an outermost sensor.

In one or more exemplary monitor devices, the first primary connection criterion based on a quality of the primary connection is not satisfied when it is determined that the quality of the primary connection is not above a first primary connection threshold.

The first primary connection criterion not being satisfied may indicate that the primary connection is lost or that the primary connection has a low quality or does not have a satisfactory quality to transmit primary monitor data to the primary accessory device. In other words, the monitor device is optionally configured to transmit secondary monitor data upon determination of no or low-quality primary connection to the primary accessory device. For example, the first primary connection criterion, also denoted CC_1_1, may be based on a first primary connection parameter, CP_1_1, associated with the primary connection and being indicative of a quality of the primary connection.

The first primary connection criterion CC_1_1 may be given as:

$$CC\_1\_1: CP\_1\_1 < TH\_C\_1\_1,$$

wherein CP_1_1 is the first primary connection parameter and TH_C_1_1_is a first primary connection threshold. The first primary connection parameter CP_1_1 may be a signal strength indicator, such as a received signal strength indicator (RSSI) or a received channel power indicator (RCPI). The first primary connection parameter CP_1_1 may be a signal-to-noise ratio.

The first primary connection criterion CC_1_1 may be given as:

$$CC\_1\_1: CP\_1\_1 < TH\_C\_1\_1,$$

wherein CP_1_1 is the first primary connection parameter indicative of errors in the primary connection (large number of errors indicating no or poor connection), such as an error rate (such as a bit error rate or a frame error rate), a number of non-acknowledgements (NACKs), and/or a number of retransmissions, and TH_C_1_1 is a first primary connection threshold.

In one or more exemplary monitor devices, to determine whether a first primary connection criterion, e.g. based on a quality of the primary connection, is satisfied may comprise to determine or obtain a first primary connection parameter, CP_1_1, e.g. based on one or more connection parameters, and to compare the first primary connection parameter with a first primary connection threshold TH_C_1_1.

The first primary connection parameter may be based on one or more connection parameters, such as signal-to-noise ratio, an error rate (such as a bit error rate, and/or a frame error rate), a number of non-acknowledgements (NACKs), and/or a number of retransmissions. In one or more exemplary monitor devices, in accordance with a determination that the first primary connection criterion is not satisfied, the monitor device does not transmit primary monitor data any longer or forgo to transmit primary monitor data to the primary accessory device. In other words, the monitor device may be configured to determine whether the primary connection to the primary accessory device is lost by determining whether the first primary connection criterion based on the quality of the primary connection is satisfied. Stated differently, the first primary connection criterion based on a quality of the primary connection is not satisfied when it is determined that the quality of the primary connection is degraded (e.g. poor) and/or reduced, leading to a loss of primary connection to the primary accessory device. Thus, the monitor device is configured to transmit secondary monitor data in case the primary connection to the primary accessory device is of low quality, e.g. lost or degraded.

The monitor device may be configured to, in accordance with a determination that the first primary connection criterion is not satisfied, determine the secondary monitor data. The secondary monitor data may be indicative of the primary connection being lost and/or degraded.

In one or more exemplary monitor devices, the monitor device is configured to, in accordance with a determination that the first primary connection criterion is not satisfied, forgo to transmit primary monitor data to the primary accessory device.

In one or more exemplary monitor devices, the monitor device is configured to, in accordance with a determination that the first primary connection criterion is not satisfied, establish a secondary connection to the secondary accessory device, wherein the secondary monitor data are transmitted via the secondary connection. To establish a secondary connection may comprise to activate an idle or inactive secondary connection.

In one or more exemplary monitor devices, the monitor device is configured to, in accordance with a determination that the first primary connection criterion is not satisfied, determine the secondary monitor data. For example, a processing, power, and/or memory capability of the secondary accessory device may be less than a processing, power, and/or memory capability of the primary accessory device, such that the secondary monitor data may need to be less/simpler than the primary monitor data.

The primary monitor data transmitted to the primary accessory device may comprise appliance data that are not transmitted to the secondary accessory device, i.e. the primary monitor data may comprise appliance data, such as one or more of second appliance data, third appliance data, fourth appliance data, and fifth appliance data, that are not included in the secondary monitor data. For example, appliance sensor data obtained from or derived from one or more appliance sensors being part of primary monitor data transmitted to the primary accessory device may not be part of secondary monitor data transmitted to the secondary accessory device. Accordingly, the secondary monitor data may be a reduced data set compared to the primary monitor data that are transmitted to the primary accessory device via the primary connection. Thereby, optimum or improved usage of possible limited capacity in the secondary accessory device is provided.

The secondary monitor data may comprise compressed appliance sensor data, such as compressed appliance sensor data for one or more sensors that are not regarded as critical, such as an inner sensor of an ostomy appliance or wound dressing. Appliance sensor data for one or more sensors that are not regarded as critical may be omitted in the secondary monitor data.

In one or more exemplary monitor devices, to determine the secondary monitor data is based on a type of the secondary accessory device, such as a smartphone, smartwatch, or tablet. Thereby, the monitor device may be able to customize the secondary monitor data transmitted to the secondary accessory device, such as by taking into account processing, power, and/or memory capabilities of the secondary accessory device. Thus, the monitor device is able to optimize transmission of monitor data.

In one or more exemplary monitor devices, to determine the secondary monitor data comprises selecting first secondary monitor data as the secondary monitor data in accordance with the secondary accessory device being a first type and selecting second secondary monitor data as the secondary monitor data in accordance with the secondary accessory device being a second type. The first secondary monitor data may be different from the second secondary monitor data. For example, the first secondary monitor data may be larger than and/or transmitted at higher frequency than the second secondary monitor, e.g. in case the first type is a smartphone and the second type is a smartwatch.

The monitor device may be configured to transmit the primary monitor data according to a primary transmission scheme and to transmit the secondary monitor data according to a secondary transmission scheme. The primary transmission scheme may be different from the secondary transmission scheme.

In one or more exemplary monitor devices, the first transmission scheme comprises a first transmission parameter. In one or more exemplary monitor devices, the second transmission scheme comprises a second transmission parameter. In one or more exemplary monitor devices, the first transmission parameter and the second transmission parameter are different. A transmission parameter may comprise a transmission frequency, a transmission periodicity, a transmission signal phase, a transmission power, a transmission radio frequency, a transmission protocol (e.g. Bluetooth, Bluetooth Low Energy, ZigBee, WLAN, cellular protocol) and/or any combination thereof.

In one or more exemplary monitor devices, to determine the secondary monitor data is based on an operating state of the personal care appliance. For example, a first operating state of the personal care appliance, e.g. requiring high attention, may trigger selection of first secondary monitor data as the secondary monitor data, while a second operating state, e.g. requiring no or little attention, may trigger selection of second secondary monitor data as the secondary monitor data, wherein the first secondary monitor data has larger size and/or frequency than the second secondary monitor data.

In one or more exemplary monitor devices, the monitor device is configured to determine whether a second primary connection criterion based on a quality of the primary connection is satisfied. In accordance with a determination that the second primary connection criterion is satisfied, the monitor device is optionally configured to resume to transmit primary monitor data to the primary accessory device. In one or more exemplary monitor devices, the monitor device is configured to, in accordance with a determination that the second primary connection criterion is satisfied, notify the secondary accessory device that the primary connection has been resumed/re-established, e.g. by including a primary connection notifier in the secondary monitor data.

In one or more exemplary monitor devices, the second primary connection criterion based on a quality of the primary connection is satisfied when it is determined that the quality of the primary connection is above a second primary connection threshold or when it is determined that the primary connection is resumed.

In one or more exemplary monitor devices, the monitor device is configured to, in accordance with a determination that the second primary connection criterion is satisfied, forgo to transmit secondary monitor data to the secondary accessory device and/or one or more of terminate, idle or inactivate the secondary connection.

The second primary connection criterion being satisfied may indicate that the primary connection is resumed or that the primary connection has a satisfactory quality to transmit primary monitor data to the primary accessory device. In other words, the monitor device is optionally configured to transmit primary monitor data upon determination of resumed primary connection to the primary accessory device. For example, the second primary connection criterion, also denoted CC_1_2, may be based on a second primary connection parameter, CP_1_2, associated with the primary connection and being indicative of a quality of the primary connection.

The second primary connection criterion CC_1_2 may be given as:

$$CC\_1\_2: CP\_1\_2 < TH\_C\_1\_2,$$

wherein CP_1_2 is the second primary connection parameter and TH_C_1_2_is a second primary connection threshold. The second primary connection parameter CP_1_2 may be a signal strength indicator, such as a received signal strength indicator (RSSI) or a received channel power indicator (RCPI). The second primary connection parameter CP_1_2 may be a signal-to-noise ratio.

The second primary connection criterion CC_1_2 may be given as:

$$CC\_1\_2: CP\_1\_2 < TH\_C\_1\_2,$$

wherein CP_1_2 is the second primary connection parameter indicative of errors in the primary connection (large number of errors indicating no or poor connection), such as an error rate (such as a bit error rate or a frame error rate), a number of non-acknowledgements (NACKs), and/or a number of retransmissions, and TH_C_1_2 is a second primary connection threshold.

In one or more exemplary monitor devices, to determine whether a second primary connection criterion, e.g. based on a quality of the primary connection, is satisfied may comprise to determine or obtain a second primary connection parameter, CP_1_2, e.g. based on one or more connection parameters, and to compare the second primary connection parameter with a second primary connection threshold TH_C_1_2.

The second primary connection parameter may be based on one or more connection parameters, such as signal-to-noise ratio, an error rate (such as a bit error rate, and/or a frame error rate), a number of non-acknowledgements (NACKs), and/or a number of retransmissions. In one or more exemplary monitor devices, in accordance with a determination that the second primary connection criterion is satisfied, the monitor device does not transmit secondary monitor data any longer or forgoes to transmit secondary monitor data to the secondary accessory device. In other words, the monitor device may be configured to determine whether the primary connection to the primary accessory device is resumed or increased in quality by determining whether the second primary connection criterion based on the quality of the primary connection is satisfied. For example, the second primary connection criterion based on a quality of the primary connection is not satisfied when it is determined that the quality of the primary connection remains lost, degraded (e.g. poor) and/or reduced.

In one or more exemplary monitor devices, the primary monitor data comprises primary appliance data, such as primary ostomy data obtained from an ostomy appliance being the personal care appliance via the first interface. In one or more exemplary monitor devices, the secondary monitor data comprises secondary appliance data, such as secondary ostomy data obtained from an ostomy appliance being the personal care appliance via the first interface.

In one or more exemplary monitor devices, the primary monitor data comprises primary appliance data, such as primary wound dressing data obtained from a wound dressing being the personal care appliance via the first interface. In one or more exemplary monitor devices, the secondary monitor data comprises secondary appliance data, such as secondary wound dressing data obtained from a wound dressing being the personal care appliance via the first interface. The secondary monitor data may be the same as the primary monitor data, i.e. the secondary monitor data may have the same configuration as the primary monitor data.

The monitor device may be configured to transmit secondary monitor data via a network to a sink device, such as a server device or the primary accessory device. The network may be a multi-hop network, such as a mesh network. For example, the monitor device may be configured to transmit secondary monitor data via one or more relay devices, such as beacons or electronic devices configured to act as a relay.

The monitor device may be configured, in accordance with a determination that the first primary connection criterion is not satisfied, store primary monitor data in the memory according to a primary storing scheme.

A storing scheme optionally defines one or more storing parameters, such as a storing frequency and/or a data size of monitor data stored in a storing operation, for storing monitor data in the memory. A storing scheme optionally defines one or more parts of monitor data to be stored in accordance with the storing scheme. The primary storing scheme may define a primary storing frequency for storing primary monitor data in the memory according to the primary storing scheme. The primary storing scheme may define a primary data size of primary monitor data stored in a storing operation in the memory according to the primary storing scheme.

In one or more exemplary monitor devices, the monitor device is configured to, in accordance with a determination that the first primary connection criterion is not satisfied, select or determine the primary storing scheme, e.g. from a plurality of storing schemes. The plurality of storing schemes may comprise two, three, four, or more storing schemes, such as at least five storing schemes. The plurality of storing schemes comprises a first storing scheme and a second storing scheme.

The secondary monitor data may comprise compressed appliance sensor data, such as compressed appliance sensor data for one or more sensors that are not regarded as critical, such as an inner sensor of an ostomy appliance or wound dressing. Appliance sensor data for one or more sensors that are not regarded as critical may be omitted in the secondary monitor data. For example, the primary monitor data may comprise appliance sensor data, such as one or more of second appliance sensor data, third appliance sensor data, fourth appliance sensor data, and fifth appliance sensor, that are not included in the secondary monitor data transmitted to the secondary accessory device.

Further, a method of operating a monitor device for a personal care system comprising a personal care appliance, the monitor device, a primary accessory device, and a secondary accessory device is disclosed, the monitor device comprising a processor; a memory connected to the processor; a first interface connected to the processor, the first interface configured for connecting the monitor device to the personal care appliance; and a second interface comprising a transceiver module connected to the processor and configured for connecting the monitor device to the primary accessory device and/or the secondary accessory device, the method comprising establishing a primary connection between the monitor device and the primary accessory device; transmitting primary monitor data to the primary accessory device via the primary connection; determining whether a first primary connection criterion based on a quality of the primary connection is satisfied; and in accordance with a determination that the first primary connection criterion is not satisfied, transmitting secondary monitor data, e.g. to the secondary accessory device.

In one or more methods of operating a monitor device, the first primary connection criterion is not satisfied when determining that the quality of the primary connection is not above a first primary connection threshold.

In one or more methods of operating a monitor device, the method comprises, in accordance with a determination that the first primary connection criterion is not satisfied, forgo transmitting primary monitor data to the primary accessory device.

In one or more methods of operating a monitor device, the method comprises, in accordance with a determination that the first primary connection criterion is not satisfied, establishing a secondary connection to the secondary accessory device, wherein the secondary monitor data are transmitted via the secondary connection.

In one or more methods of operating a monitor device, the method comprises, in accordance with a determination that the first primary connection criterion is not satisfied, determining the secondary monitor data.

In one or more methods of operating a monitor device, determining the secondary monitor data is based on a type of the secondary accessory device.

In one or more methods of operating a monitor device, determining the secondary monitor data comprises selecting first secondary monitor data as the secondary monitor data in accordance with the secondary accessory device being a first type and selecting second secondary monitor data as the secondary monitor data in accordance with the secondary accessory device being a second type.

In one or more methods of operating a monitor device, determining the secondary monitor data is based on an operating state of the personal care appliance.

In one or more methods of operating a monitor device, the method comprises determining whether a second primary connection criterion based on a quality of the primary connection is satisfied; and in accordance with a determination that the second primary connection criterion is satisfied, resume transmitting primary monitor data to the primary accessory device.

In one or more methods of operating a monitor device, the second primary connection criterion based on a quality of the primary connection is satisfied when it is determined that the quality of the primary connection is above a second primary connection threshold or when it is determined that the primary connection is resumed.

In one or more methods of operating a monitor device, the method comprises, in accordance with a determination that the second primary connection criterion is satisfied, forgo transmitting secondary monitor data to the secondary accessory device.

In one or more methods of operating a monitor device, the personal care appliance is an ostomy appliance, and the method comprising obtaining ostomy data from the ostomy appliance and including the ostomy data in the primary monitor data and/or in the secondary monitor data.

In one or more methods of operating a monitor device, the personal care appliance is a wound dressing, and the method comprising obtaining wound dressing data from the wound dressing and including the wound dressing data in the primary monitor data and/or in the secondary monitor data.

Also disclosed is a computer readable storage medium storing one or more programs, the one or more programs comprising instructions, which when executed by a monitor device with an interface, a memory and a processor cause the monitor device to be configured to operate in accordance with methods of operating a monitor device as described herein.

In one or more exemplary methods of operating a monitor device, the method comprises, in accordance with a determination that the first primary connection criterion is not satisfied, storing primary monitor data in the memory according to a primary storing scheme.

In one or more exemplary methods of operating a monitor device, the method comprising, in accordance with a determination that the first primary connection criterion is not satisfied, selecting or determining the primary storing scheme, e.g. from a plurality of storing schemes.

It is to be noted that descriptions of the monitor device being configured to perform acts also apply to the corresponding acts in the method of operating a monitor device and vice versa.

The present disclosure provides an accessory device (primary accessory device) for a personal care system, the personal care system comprising a personal care appliance, a monitor device, a primary accessory device, and a secondary accessory device, wherein the accessory device is configured as the primary accessory device, the primary accessory device comprising a processor; a memory connected to the processor; and an interface configured to connect the primary accessory device to the monitor device of the personal care system, the interface comprising a transceiver module connected to the processor, wherein the primary accessory device is configured to establish a primary connection between the monitor device and the primary accessory device; receive primary monitor data from the monitor device; optionally establish an accessory connection between the primary accessory device and the secondary accessory device; and determine whether a first primary connection criterion based on a quality of the primary connection is satisfied. The primary accessory device is optionally configured to, in accordance with a determination that the first primary connection criterion is not satisfied, receive secondary accessory data from the secondary accessory device; and/or communicate or transmit a primary indication, e.g. included in primary accessory data to the secondary accessory device.

The primary accessory device is optionally configured to, in accordance with a determination that the first primary connection criterion is not satisfied, transmit primary accessory data to the secondary accessory device. Thereby the primary accessory device may be configured to inform the secondary accessory device on historical monitor data and/or current or previous operating states of the personal care appliance, in turn enabling the secondary accessory device more precise operating state determinations and/or secondary indications.

Also disclosed is an accessory device (secondary accessory device) for a personal care system, the personal care system comprising a personal care appliance, a monitor device, a primary accessory device, and a secondary accessory device, wherein the accessory device is configured as the secondary accessory device, the secondary accessory device comprising a processor; a memory connected to the processor; and an interface configured to connect the secondary accessory device to the monitor device of the personal care system, the interface comprising a transceiver module connected to the processor, wherein the secondary accessory device is configured to establish a secondary connection between the monitor device and the secondary accessory device; receive, from the monitor device, secondary monitor data, indicative of a primary connection between the monitor device and the primary accessory device; and optionally communicate a secondary indication based on the secondary monitor data.

The secondary monitor data may be indicative of a primary connection between the monitor device and the primary accessory device being lost or degraded.

In one or more (secondary) accessory devices, the secondary indication is indicative of a first primary connection criterion not being satisfied in the monitor device and/or in the primary accessory device.

In one or more exemplary secondary accessory devices, the secondary accessory device is configured to select, from a plurality of indications, the secondary indication indicative of the quality of the primary connection. In one or more exemplary secondary accessory devices, the secondary indication is indicative of the operating state at a time where the monitor device and/or the primary accessory device determines that a primary criterion based on the quality of the primary connection is not satisfied. For example, the secondary indication may be indicative of the operating state at a time where the primary connection is lost and/or degraded and/or interrupted. The secondary accessory device is optionally configured to, e.g. in accordance with receiving secondary monitor data indicative of the primary connection being lost or degraded, determine, such as select, obtain, and/or generate, the secondary indication indicative of the quality of the primary connection. For example, the secondary indication may be indicative of the operating state of the personal care appliance at a time where the primary connection is lost and/or degraded and/or interrupted.

In one or more (secondary) accessory devices, the secondary accessory device is configured to determine an operating state of the personal care appliance based on the secondary monitor data, and wherein the secondary indication is based on the operating state.

In one or more (secondary) accessory devices, the secondary accessory device is configured to establish an accessory connection between the primary accessory device and the secondary accessory device; receive primary accessory data from the primary accessory device; and determine the secondary indication based on the primary accessory data.

For example, the secondary accessory device is configured to, e.g. based on the secondary monitor data and/or primary accessory data, communicate the secondary indication, e.g. to the user, e.g. via an output device (such as a display and/or a loudspeaker) of the secondary accessory device. In one or more exemplary embodiments, the secondary indication may be communicated by sound.

In one or more (secondary) accessory devices, the secondary accessory device is configured to establish an accessory connection between the primary accessory device and the secondary accessory device; and transmit secondary accessory data to the primary accessory device. The secondary accessory data may be based on or include the secondary monitor data and/or the secondary indication. The secondary accessory device may be configured to transmit secondary accessory data to the primary accessory device directly and/or via a network. The network may be a multi-hop network, such as a mesh network. For example, the secondary accessory device may be configured to transmit secondary accessory data via one or more relay devices, such as beacons or electronic devices configured to act as a relay.

In one or more (secondary) accessory devices, the secondary accessory device is configured to, in accordance with a determination that a primary connection between the monitor device and the primary accessory device has been resumed, forgo to receive secondary monitor data from the monitor device. Accordingly, the secondary accessory device may be configured to determine whether a primary connection between the monitor device and the primary accessory device has been resumed/re-established, e.g. based on the secondary monitor data and/or based on primary accessory data.

The secondary accessory device may be configured to store the secondary monitor data, and, e.g. in accordance with establishing an accessory connection between the primary accessory device and the secondary accessory device, include the secondary monitor data in secondary accessory data and transmit the secondary accessory data including the secondary monitor data to the primary accessory device. Accordingly, the secondary accessory device may be configured to determine whether an accessory connection between the primary accessory device and the secondary accessory device has been established. Thereby, the secondary accessory device may function as a storage and/or relay device to ensure that essential system data, such as appliance data, are not lost in case of a lost primary connection. Such functionality may in particular be useful in cases where the processing resources of the secondary accessory device are limited, e.g. in a scenario where the secondary accessory device is a smartwatch having less processing resources than the primary accessory device, e.g. being a smartphone.

In one or more (secondary) accessory devices and/or methods of operating a secondary accessory device, the secondary accessory device is a smartphone.

In one or more (secondary) accessory devices and/or methods of operating a secondary accessory device, the secondary accessory device is a smartwatch.

In one or more (secondary) accessory devices and/or methods of operating a secondary accessory device, the secondary accessory device is a tablet.

The secondary accessory device may be configured to determine an operating state of the personal care appliance based on the secondary monitor data. The secondary accessory device may be configured to determine the secondary indication based on the operating state of the personal appliance. The secondary accessory device may be configured to include operating state(s) determined based on the secondary monitor data in the secondary accessory data.

The disclosed secondary accessory device is capable of determining and/or communicating a secondary indication indicative of a quality of a primary connection between the monitor device and the primary accessory device. The present disclosure improves the reliability of the monitoring performed by the personal care system, by communicating the secondary indication indicative of the quality of primary connection when a quality of the primary connection is not satisfactory. This permits to notify appropriately the user about missing primary connection and activate or utilize the secondary accessory device in the monitoring of the personal care appliance.

For example, communication of the second indication indicative of a quality of the primary connection to the monitor device assists the user in monitoring the personal care appliance by informing the user that the primary accessory device is not active and/or that the secondary accessory device has taken over monitoring the personal care appliance, in turn providing a reliable and secure monitoring of the personal care appliance and operating state thereof. Thus, the present disclosure helps reducing the risk of a user experiencing a leakage (e.g. output leakage between a user's skin and the baseplate of the ostomy appliance) from an ostomy appliance in a planned activity or helps reducing the risk of a user experiencing a wet wound due to saturated fluid in an absorbent core layer of a wound dressing appliance. In particular, determination and/or communication of the second indication indicative of an estimated operating state, and possibly with a latest operating state, according to the present disclosure is performed based on secondary monitor data and/or primary accessory data indicative of a condition of the personal care appliance which may not be visible to the user.

It is an advantage of the present disclosure that a user of a personal care appliance or a health care professional is able to monitor and plan the use of the personal care appliance with daily life. In particular, a user is informed about non-presence of the primary accessory device and is able to act accordingly, e.g. by accepting use of the secondary accessory device or returning to be within range of the primary accessory device.

For example, the primary accessory device may be configured to, in accordance with a determination that the first primary connection criterion is not satisfied, communicate the secondary indication to the secondary accessory device as primary accessory data.

In one or more exemplary primary accessory devices, the first primary connection criterion based on a quality of the connection is not satisfied when it is determined that the quality of the connection is not above a first primary connection threshold.

In one or more exemplary secondary accessory devices, to select the secondary indication indicative of the quality of the primary connection optionally comprises to determine an estimated operating state of the personal care appliance, e.g. based on one or more previous operating states of the personal care appliance as indicated by primary accessory data received from the primary accessory device. The one or more previous operating states of the personal care appliance are determined and optionally transmitted by the primary accessory device before the time where the first primary connection criterion based on the quality of the connection is not satisfied (e.g. before the time where the primary connection is lost).

In one or more exemplary secondary accessory devices, to determine the estimated operating state of the personal care appliance based on one or more previous operating states of the personal care appliance comprises to predict the estimated operating state of the personal care appliance based on one or more previous operating states of the personal care appliance. In one or more exemplary secondary accessory devices, the secondary indication is indicative of the estimated operating state.

The processor of the secondary accessory device may be configured to determine the estimated operating state based on one or more previous operating states, such as based on one or more operating states previously determined by the primary accessory device (i.e. prior to loss/degradation of connection). Optionally, one or more operating states previously determined by the accessory device may relate the different personal care appliances as the one currently used by the user, which have the characteristics and/or components which are the same as the one currently used by the user.

The processor of the secondary accessory device may be configured to determine the estimated operating state as a future operating state of the personal care appliance based on one or more previous operating states, such as based on one or more (future and/or current) operating states previously determined by the primary accessory device and/or the secondary accessory device.

It may be envisaged that the processor of the secondary accessory device may be configured to predict the estimated operating state of the personal care appliance by deriving a trend or a function of an operating state and/or the secondary monitor data over the time period, e.g. for the similar personal care appliances as the one currently used by the user, or for similar base plates as the currently used one. The time period may include a time period up to and possibly including a current time. The time period may include a time period from a start time of use of any personal care appliances, to the current time of determination of the estimated operating state. The time period may include a time period from a start time of the loss of connection to the current time. The time period may include a time window that periodically occurs, such as a morning time period, an afternoon time period, a night time period, a daily time period, a weekly time period, etc.

The processor of the secondary accessory device may be configured to predict the estimated operating state based on a parameter characterizing a product type of the personal care appliance. The processor of the secondary accessory device may be configured to predict (such as to determine) the estimated operating state based on secondary monitor data obtained for similar product types of personal care appliances previously used by the user.

In one or more exemplary accessory devices, the secondary accessory device is configured to, in accordance with a determination that the primary connection has been lost or degraded, communicate the secondary indication indicative of the quality of the connection, by displaying, on a display of the secondary accessory device, a first user interface object representative of the secondary indication. The secondary user interface object may be displayed as one or more media, such as text, graphic and/or video.

The secondary accessory device may comprise the display configured to display a user interface. The display may comprise a touch sensitive surface. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the secondary accessory device may be configured to detect touch (e.g. the display is a touch-sensitive display), the input comprises a contact on the touch sensitive display. A touch-sensitive display provides an input interface and an output interface between the accessory device and a user. A processor of the secondary accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user interface objects.

The processor of the secondary accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the personal care appliance.

In one or more exemplary secondary accessory devices, to communicate the secondary indication comprises to display, on a visual interface (e.g. a display) of the accessory device, a user interface comprising a user interface object representative of the secondary indication, such as a first user interface object representative of the secondary indication indicative of the quality of the primary connection and/or representative of a first operating state of the personal care appliance, and/or representative of a second operating state of the personal care appliance.

In one or more exemplary secondary accessory devices, the first user interface object representative of the secondary indication comprises a first primary user interface object representative of the secondary indication, and/or a first primary user interface object representative of one or more operating states.

For example, the first user interface object may comprise one or more visual indicators representative of the secondary indication, such as a first visual indicator, a second visual indicator, a third visual indicator. For example, the visual indicator may be in a shape characterizing the personal care appliance. The visual change may be performed by a change of one or more of: colour, shape, blurring, and animation. For example, the visual indicators may be a text prompt indicating to the user the dynamic internal operating state of the personal care appliance.

In one or more exemplary secondary accessory devices, to communicate the secondary indication comprises to notify the user via the interface, such as by displaying a notification on a display of the accessory device. The notification may comprise the first user interface object representative of the secondary indication. The notification may comprise a notification indicator to open an application related to the personal care appliance. The secondary accessory device may be configured to detect an input on the notification indicator. The secondary accessory device may be configured to, in response to the input, opening the application related to the personal care appliance. The secondary accessory device may be configured to, in response to the opening of the application, to display a user interface object representative of an operating state (such as a latest operating state and/or an estimated operating state). For example, the first user interface object may convey: "Connection to primary accessory device lost" and/or "everything is good".

In one or more exemplary secondary accessory devices, the secondary accessory device is configured to determine whether the primary connection has been resumed/re-established, e.g. based on the secondary monitor data and/or primary accessory data.

In one or more exemplary secondary accessory devices, the secondary accessory device is configured to in accordance with a determination that the primary connection is resumed or has increased quality, communicate a tertiary indication indicative of the quality of the primary connection. In one or more exemplary secondary accessory devices, the secondary accessory device is configured to in accordance with a determination that the primary connection has been resumed, determine the tertiary indication.

The secondary accessory device is optionally configured to, in accordance with a determination that the primary connection is resumed or has increased quality, determine, such as select, obtain, and/or generate, the tertiary indication indicative of the quality of the primary connection. For example, the tertiary indication may be indicative of an operating state based on secondary monitor data received from the monitor device at the time that the primary connection has been resumed, such as based on secondary monitor data stored in the monitor device.

In one or more exemplary secondary accessory devices, the tertiary indication is indicative of the operating state at a time where the primary connection is resumed or has increased quality. For example, the tertiary indication may be indicative of the operating state at a time where the primary connection is resumed, such as re-established.

In one or more exemplary secondary accessory devices, the secondary monitor data comprises ostomy data obtained from an ostomy appliance being the personal care appliance via the interface or wound dressing data obtained from a wound dressing being the personal care appliance via the interface.

In one or more exemplary secondary accessory devices, the secondary accessory device is configured to, in accordance with a determination that the primary connection is resumed or has increased quality, communicate the tertiary indication indicative of the quality of the primary connection, by displaying, on the display of the accessory device, a second user interface object representative of the tertiary indication. For example, the second user interface object may convey: "Connection to primary accessory device resumed" and/or "everything is still good". For example, to communicate the tertiary indication may comprise to notify the user via the interface, such as by displaying a notification indicative of the tertiary indication on a display of the secondary accessory device.

The present disclosure provides a method of operating a secondary accessory device for a personal care system. The personal care system comprises a personal care appliance, a monitor device, a primary accessory device, and the secondary accessory device. The method comprises establishing a secondary connection between the monitor device and the secondary accessory device. The method comprises receiving secondary monitor data from the monitor device. The method optionally comprises determining an operating state of the personal care appliance based on the secondary monitor data. The method comprises communicating a secondary indication based on the secondary monitor data and optionally indicative of the quality of the primary connection, such as indicative of a first primary connection criterion not being satisfied in the monitor device and/or in the primary accessory device.

In one or more exemplary methods of operating a secondary accessory device, the method comprises selecting, from a plurality of indications, the secondary indication indicative of the quality of the primary connection.

In one or more exemplary methods of operating a secondary accessory device, communicating the secondary indication indicative of the quality of the primary connection comprises displaying, on a display of the accessory device, a first user interface object representative of the secondary indication.

In one or more exemplary methods of operating a secondary accessory device, selecting the secondary indication indicative of the quality of the primary connection comprises determining an estimated operating state of the personal care appliance based on one or more previous operating states of the personal care appliance.

In one or more exemplary methods of operating a secondary accessory device, determining the estimated operating state of the personal care appliance based on the one or more previous operating states of the personal care appliance comprises predicting the estimated operating state of the personal care appliance based on the one or more previous operating states of the personal care appliance.

In one or more exemplary methods of operating a secondary accessory device, the secondary indication is indicative of the operating state at a time where the primary connection is lost or degraded.

In one or more exemplary methods of operating a secondary accessory device, the secondary indication is indicative of the estimated operating state.

In one or more exemplary methods of operating a secondary accessory device, the method comprises determining whether the primary connection has been resumed or re-established, e.g. based on the secondary monitor data and/primary accessory data.

In one or more exemplary methods of operating a secondary accessory device, the method comprises, in accordance with a determination that the primary connection has been resumed or re-established, communicating a tertiary indication indicative of the quality of the primary connection.

In one or more exemplary methods of operating a secondary accessory device, the tertiary indication is indicative of the operating state at a time where the primary connection has been resumed or re-established. For example, the tertiary indication is optionally indicative of the operating state at a time where the primary connection is resumed, such as re-established.

In one or more exemplary methods of operating a secondary accessory device, the secondary monitor data comprises ostomy data obtained from an ostomy appliance being the personal care appliance via the interface or wound dressing data obtained from a wound dressing being the personal care appliance via the interface.

In one or more exemplary methods of operating a secondary accessory device, communicating the tertiary indication indicative of the quality of the connection comprises displaying, on the display of the accessory device, a second user interface object representative of the tertiary indication.

Is to be noted that descriptions of the secondary accessory device being configured to perform acts also apply to the corresponding acts in the method of operating a secondary accessory device and vice versa.

Also disclosed is a computer readable storage medium storing one or more programs, the one or more programs comprising instructions, which when executed by a secondary accessory device with an interface, a memory and a processor cause the accessory device to perform any of the methods of operating a secondary accessory device as described herein.

FIG. 1 illustrates an exemplary personal care system 1 embodied as an ostomy system 1A. The personal care system 1 (ostomy system 1A) comprises a personal care appliance 2 embodied as an ostomy appliance 2A including a base plate 4 and an ostomy pouch (not shown). Further, the personal care system 1 comprises a monitor device 6, a primary accessory device 8A (mobile telephone, smartphone), and a secondary accessory device 8B (smartwatch). The monitor device 6 is connectable to the personal care appliance 2, such as to base plate 4 and/or to an electrode assembly of or mounted to the personal care appliance 2, via respective first connectors of the monitor device 6 and base plate 4/electrode assembly. The monitor device 6 is configured for wireless communication via primary connection 9A with the primary accessory device 8A and via secondary connection 9B with the secondary accessory device 8B. Optionally, the primary accessory device 8A and/or secondary accessory device 8B are configured to communicate with a server device 10 of the personal care system 1, e.g. via network 12. The primary accessory device 8A and the secondary accessory device 8B may be wirelessly connected via accessory connection 9C. The primary accessory device 8A and the secondary accessory device 8B may be wirelessly connected via network 12. The server device 10 may be operated and/or controlled by the ostomy appliance manufacturer and/or a service centre. Appliance data (ostomy data in the shown ostomy system) or parameter data based on the appliance data (ostomy data in the shown ostomy system) are obtained from electrodes/sensors of electrode assembly embedded in or mounted to the personal care appliance 2 with the monitor device 6. The monitor device 6 processes the appliance data and/or parameter data based on the appliance data to determine primary monitor data that are transmitted to the primary accessory device 8A via primary connection 9A and/or secondary monitor data that are transmitted to the secondary accessory device 8B via secondary connection 9B. In the illustrated personal care system, the primary accessory device 8A is a mobile phone, however the primary accessory device 8A may be embodied as another handheld device, such as a tablet device, or a wearable, such as a watch or other wrist-worn electronic device. In the illustrated personal care system, the secondary accessory device 8B is a smartwatch, however the secondary accessory device 8B may be embodied as another handheld device, such as a tablet device, smartphone, or a wearable, such as a watch or other wrist-worn electronic device. Accordingly, the monitor device 6 is configured to determine primary monitor data and transmit the primary monitor data to the primary accessory device 8A and/or determine secondary monitor data and transmit the secondary monitor data to the secondary accessory device 8B. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma.

The personal care system 1 optionally comprises a docking station 20 forming an accessory device of the personal care system 1. The docking station 20 comprises a docking monitor interface including a first connector 22 configured for electrically and/or mechanically connecting the monitor device 6 to the docking station 20. The docking monitor interface may be configured for wirelessly connecting the monitor device 6 to the docking station 20. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
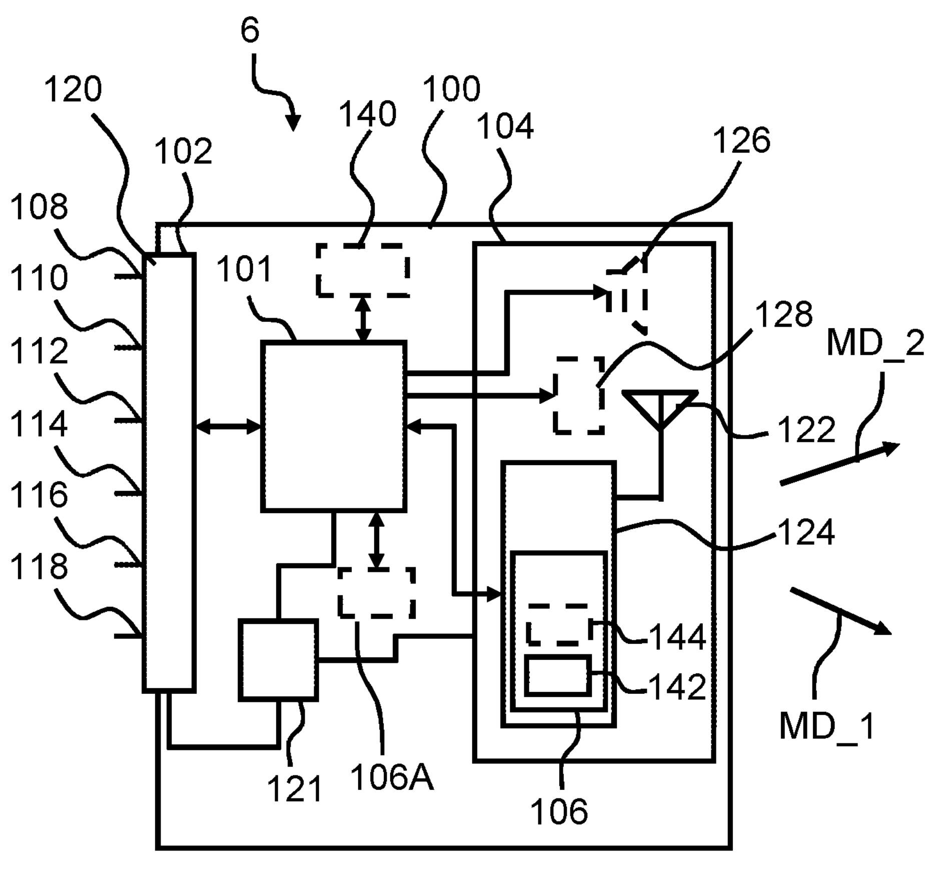
FIG. 2 illustrates an exemplary monitor device according to the present disclosure.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106/106A. The memory 106/106A is optionally connected to the processor 101. The memory 106 is embedded optionally as flash memory in the second interface 104.

Figure 8:
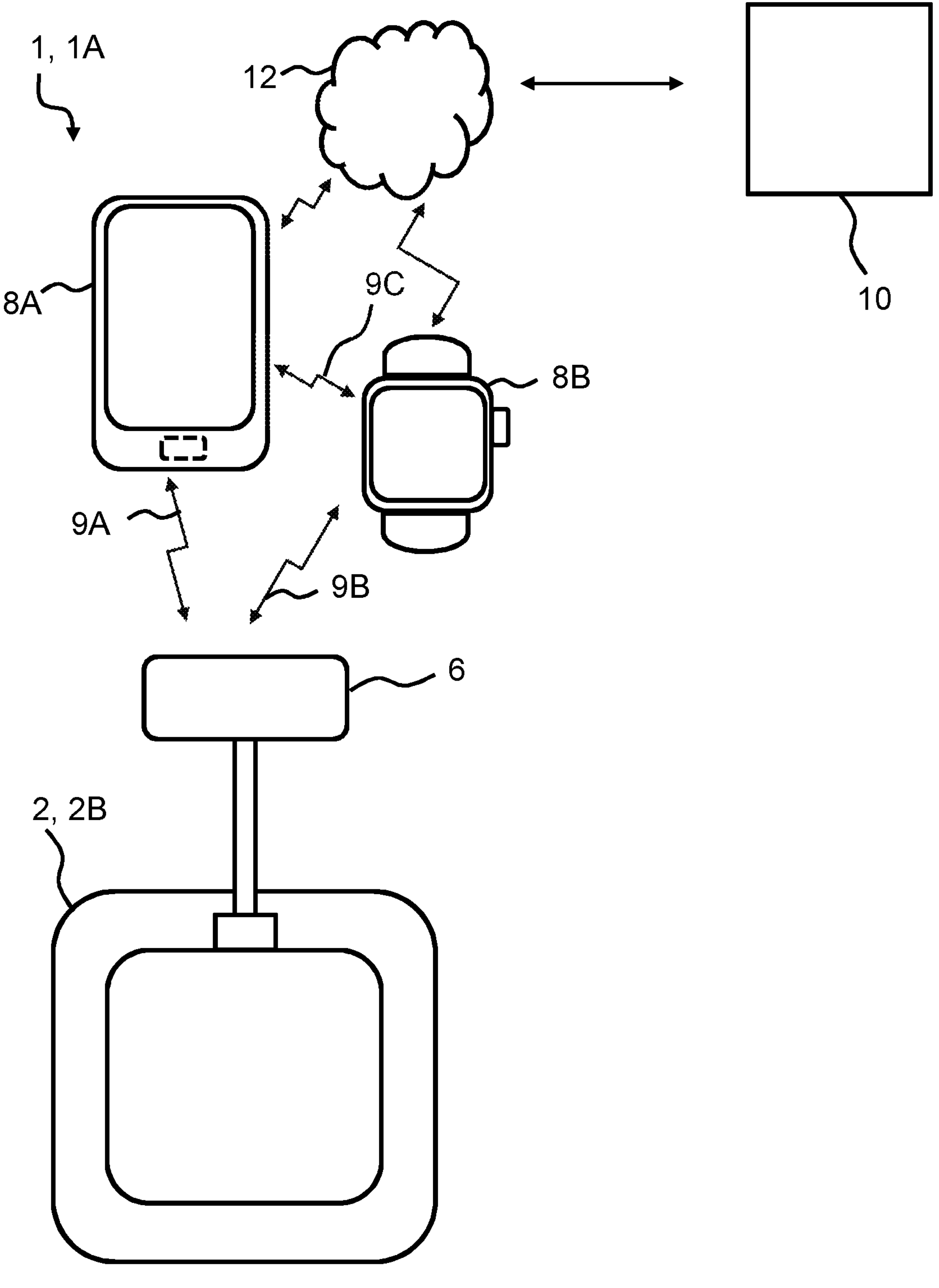
FIG. 8 illustrates an exemplary personal care system being a wound dressing system.

The first interface 102 is configured as an appliance interface for electrically and/or mechanically connecting the monitor device 6 to the personal care appliance, e.g. ostomy appliance 2A or a wound dressing appliance, see FIG. 8. The first interface 102 comprises a plurality of terminals for forming electrical connections with respective terminals of the personal care appliance 2 (electrode assembly). The first interface 102 optionally comprises between four and 20 terminals, such as between six and twelve terminals, including a ground terminal 108, a first terminal 110, a second terminal 112 and a third terminal 114. The first interface 102 optionally comprises a fourth terminal 116 and a fifth terminal 118. In one or more exemplary monitor devices, the first interface 102 optionally comprises a sixth terminal and/or a seventh terminal. The first interface 102 of the monitor device 6 comprises a coupling part 120 for forming a mechanical connection, such as a releasable coupling between the monitor device and the personal care appliance, e.g. with a base plate of an ostomy appliance and/or an electrode assembly of ostomy system/wound dressing system. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, and the second interface 104. The power unit comprises a battery and charging circuitry. The charging circuitry is connected to the battery and optionally to terminals of the first interface 102 for charging the battery via terminals of the first interface, e.g. terminals of the first connector. The charging circuitry may be configured for wireless charging of the battery.

The second interface 104 of monitor device is configured as an accessory interface for connecting the monitor device 6 to primary accessory device 8A and secondary accessory device 8B. The second interface 104 comprises an antenna 122 and a wireless transceiver 124 also denoted transceiver module, the wireless transceiver 124 connected to the processor 101 and configured for wireless communication with accessory device(s), such as configured for connecting the monitor device to the one or more accessory devices 8A, 8B of the personal care system. Optionally, the second interface 104 comprises a loudspeaker 126 and/or a haptic feedback element 128 for provision of respective audio signal and/or haptic feedback to the user. The memory 106 may be an internal memory, such as flash memory of the wireless transceiver 124. Thereby, a separate memory module can be omitted which provides a simpler and lighter/smaller monitor device.

The monitor device 6 optionally comprises a sensor unit 140 connected to the processor 101. The sensor unit 140 may comprise a temperature sensor for feeding temperature data to the processor 101 and/or a G-sensor or accelerometer for feeding acceleration data to the processor 101.

The monitor device/processor 101/transceiver module 124 is configured to establish a primary connection between the monitor device and the primary accessory device; transmit primary monitor data MD_1 to the primary accessory device via the primary connection; determine whether a first primary connection criterion based on a quality of the primary connection is satisfied; and in accordance with a determination that the first primary connection criterion is not satisfied, transmit secondary monitor data MD_2 to the secondary accessory device. The monitor device may be configured to store the primary monitor data 142 in the memory 106.

The first primary connection criterion CC_1_1 may be given as:

$$CC\_1\_1: CP\_1\_1 < TH\_C\_1\_1,$$

wherein CP_1_1 is the first primary connection parameter and TH_C_1_1_is a first primary connection threshold. The first primary connection parameter CP_1_1 may be a signal strength indicator, such as a received signal strength indicator (RSSI) or a received channel power indicator (RCPI). The first primary connection parameter CP_1_1 may be a signal-to-noise ratio. In other words, the first primary connection criterion based on a quality of the primary connection is not satisfied when it is determined that the quality of the primary connection is not above a first primary connection threshold.

The monitor device/processor 101 is optionally configured to, in accordance with a determination that the first primary connection criterion is not satisfied, forgo to transmit primary monitor data to the primary accessory device The monitor device 6 is optionally configured to, in accordance with a determination that the first primary connection criterion is not satisfied, establish a secondary connection to the secondary accessory device, wherein the secondary monitor data MD_2 are transmitted via the secondary connection. To establish a secondary connection may comprise to activate an idle or inactive secondary connection.

The monitor device 6 is optionally configured to, in accordance with a determination that the first primary connection criterion is not satisfied, determine the secondary monitor data MD_2. For example, a processing, power, and/or memory capability of the secondary accessory device may be less than a processing, power, and/or memory capability of the primary accessory device, such that the secondary monitor data may need to be less/simpler than the primary monitor data. The secondary monitor data may correspond to the primary monitor data, e.g. if the primary accessory device and the secondary accessory device are both smartphones having similar processing, power, and/or memory capabilities.

The primary monitor data transmitted to the primary accessory device may comprise appliance data that are not transmitted to the secondary accessory device, i.e. the primary monitor data may comprise appliance data, such as one or more of second appliance data, third appliance data, fourth appliance data, and fifth appliance data, that are not included in the secondary monitor data. For example, appliance sensor data obtained from or derived from one or more appliance sensors being part of primary monitor data transmitted to the primary accessory device may not be part of secondary monitor data transmitted to the secondary accessory device. Accordingly, the secondary monitor data may be a reduced data set compared to the primary monitor data that are transmitted to the primary accessory device via the primary connection. Thereby, optimum or improved usage of possible limited capacity in the secondary accessory device is provided.

The secondary monitor data may comprise compressed appliance sensor data, such as compressed appliance sensor data for one or more sensors that are not regarded as critical, such as an inner sensor of an ostomy appliance or wound dressing. Appliance sensor data for one or more sensors that are not regarded as critical may be omitted in the secondary monitor data.

In monitor device 6, to determine the secondary monitor data is optionally based on a type of the secondary accessory device, such as a smartphone, smartwatch, or tablet. Thereby, the monitor device 6 may be able to customize the secondary monitor data transmitted to the secondary accessory device, such as by taking into account processing, power, and/or memory capabilities of the secondary accessory device. Thus, the monitor device 6 is able to optimize transmission of monitor data.

The monitor device 6/processor 101 is optionally configured to determine whether a second primary connection criterion based on a quality of the primary connection is satisfied. In accordance with a determination that the second primary connection criterion is satisfied, the monitor device is optionally configured to resume to transmit primary monitor data to the primary accessory device. In one or more exemplary monitor devices, the monitor device is configured to, in accordance with a determination that the second primary connection criterion is satisfied, notify the secondary accessory device that the primary connection has been resumed/re-established, e.g. by including a primary connection notifier in the secondary monitor date. The second primary connection criterion based on a quality of the primary connection may be satisfied when it is determined that the quality of the primary connection is above a second primary connection threshold or when it is determined that the primary connection is resumed.

The monitor device 6/processor 101 is optionally configured to, in accordance with a determination that the second primary connection criterion is satisfied, forgo to transmit secondary monitor data to the secondary accessory device and/or one or more of terminate, idle or inactivate the secondary connection. Thereby a power-efficient monitor device is provided.

The second primary connection criterion being satisfied may indicate that the primary connection is resumed or that the primary connection has a satisfactory quality to transmit primary monitor data to the primary accessory device. In other words, the monitor device is optionally configured to transmit primary monitor data upon determination of resumed primary connection to the primary accessory device. For example, the second primary connection criterion, also denoted CC_1_2, may be based on a second primary connection parameter, CP_1_2, associated with the primary connection and being indicative of a quality of the primary connection.

The second primary connection criterion CC_1_2 may be given as:

$$CC\_1\_2: CP\_1\_2 < TH\_C\_1\_2,$$

wherein CP_1_2 is the second primary connection parameter and TH_C_1_2_is a second primary connection threshold. The second primary connection parameter CP_1_2 may be a signal strength indicator, such as a received signal strength indicator (RSSI) or a received channel power indicator (RCPI). The second primary connection parameter CP_1_2 may be a signal-to-noise ratio.

The processor 101 is configured to obtain appliance data based on appliance measurements via the terminals of the first interface 102. The processor 101 is configured to determine primary monitor data and/or secondary monitor data, based on the appliance data and optionally in accordance with a respective transmission scheme.

Figure 3:
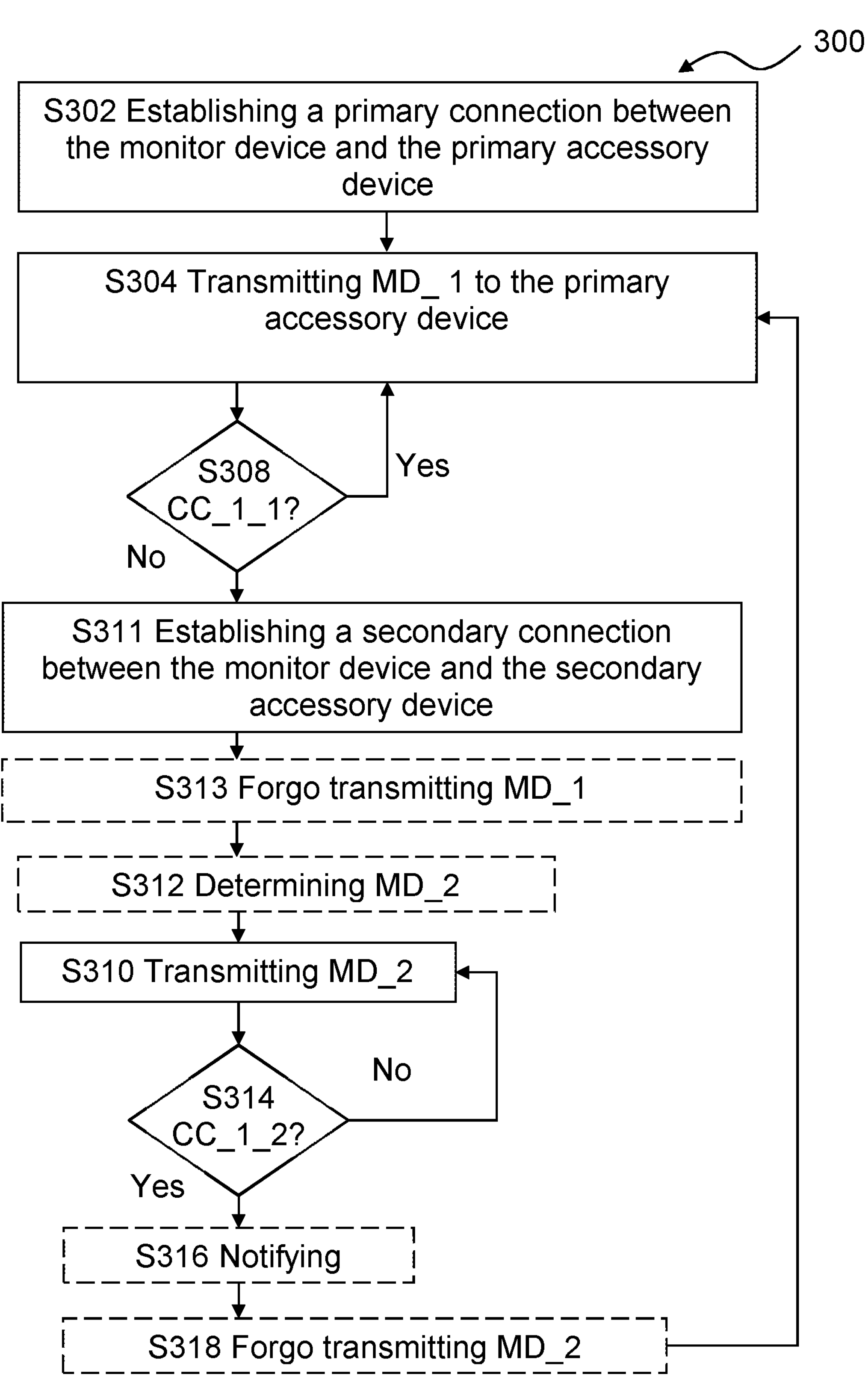
FIG. 3 is a flow diagram of an example method of operating a monitor device for a personal care system according to the present disclosure.

The processor 101 may be optionally configured to perform any of the operations disclosed in FIG. 3 (such as any one or more of S308, S310, S312, S314, S316). The operations of the accessory device 100 may be embodied in the form of executable logic routines (such as, lines of code, software programs, etc.) that are stored on a non-transitory computer readable medium (such as, internal memory in the processor 101 or external memory) and are executed by the processor 101).

Furthermore, the operations of the monitor device 100 may be considered a method that the monitor device 100 is configured to carry out. Also, while the described functions and operations may be implemented in software, such functionality may as well be carried out via dedicated hardware or firmware, or some combination of hardware, firmware and/or software.

The memory 106 and/or 106A may be one or more of a buffer, a flash memory, a hard drive, a removable media, a volatile memory, a non-volatile memory, a random access memory (RAM), or other suitable device. In a typical arrangement, the memory 106 may include a non-volatile memory for long term data storage and a volatile memory that functions as system memory for the processor 106. The memory 106, 106A may exchange data with the processor 101 over a data bus. Control lines and an address bus between the memory 101 and the processor 402 also may be present (not shown in FIG. 2). The memory 106, 106A is considered a non-transitory computer readable medium.

FIG. 3 shows a flow diagram of an example method 300 of operating a monitor device for a personal care system, such as monitor device 6 of FIG. 2.

The method 300 comprises establishing S302 a primary connection between the monitor device and the primary accessory device; optionally transmitting S304 primary monitor data MD_1 to the primary accessory device via the primary connection, determining S308 whether a first primary connection criterion CC_1_1 based on a quality of the primary connection is satisfied; and in accordance with a determination that the first primary connection criterion CC_1_1 is not satisfied, transmitting S310 secondary monitor data to the secondary accessory device.

In method 300, the act of determining S308 whether the first primary connection criterion CC_1_1 based on a quality of the primary connection is satisfied optionally comprises determining whether the quality of the connection is above a threshold, e.g. wherein the first primary connection criterion CC_1_1 may be given as: CC_1_1: CP_1_1>TH_C_1_1, wherein CP_1_1 is the first primary connection parameter being a signal strength indicator, such as a received signal strength indicator (RSSI) or a received channel power indicator (RCPI), or a signal-to-noise ratio, and TH_C_1_1_is a first primary connection threshold.

The method 300 comprises, in accordance with a determination that the first primary connection criterion CC_1_1 is not satisfied, establishing S311 a secondary connection to the secondary accessory device, wherein the secondary monitor data MD_2 are transmitted via the secondary connection.

The method 300 optionally comprises, in accordance with a determination that the first primary connection criterion CC_1_1 is not satisfied, determining S312 the secondary monitor data MD_2. The secondary monitor data MD_2 may be indicative of the primary connection being lost and/or degraded. The method 300 optionally comprises, in accordance with a determination that the first primary connection criterion CC_1_1 is satisfied, proceeding to transmitting S304 primary monitor data MD_1 to the primary accessory device via the primary connection.

The method 300 optionally comprises, in accordance with a determination that the first primary connection criterion CC_1_1 is not satisfied, forgo S313 transmitting primary monitor data MD_1 to the primary accessory device.

The method 300 optionally comprises determining S314 whether a second primary connection criterion CC_1_2 based on a quality of the primary connection is satisfied.

The method 300 optionally comprises, in accordance with a determination that the second primary connection criterion is satisfied, notifying S316 the secondary accessory device that the primary connection has been resumed/re-established, e.g. by including a primary connection notifier in the secondary monitor date.

The method optionally comprises, in accordance with a determination that the second primary connection criterion is satisfied, forgo S318 transmitting secondary monitor data MD_2 to the secondary accessory device.

In accordance with a determination that the second primary connection criterion is satisfied, the method 300 optionally comprises resuming transmitting S304 primary monitor data MD_1 to the primary accessory device.

Figure 4:
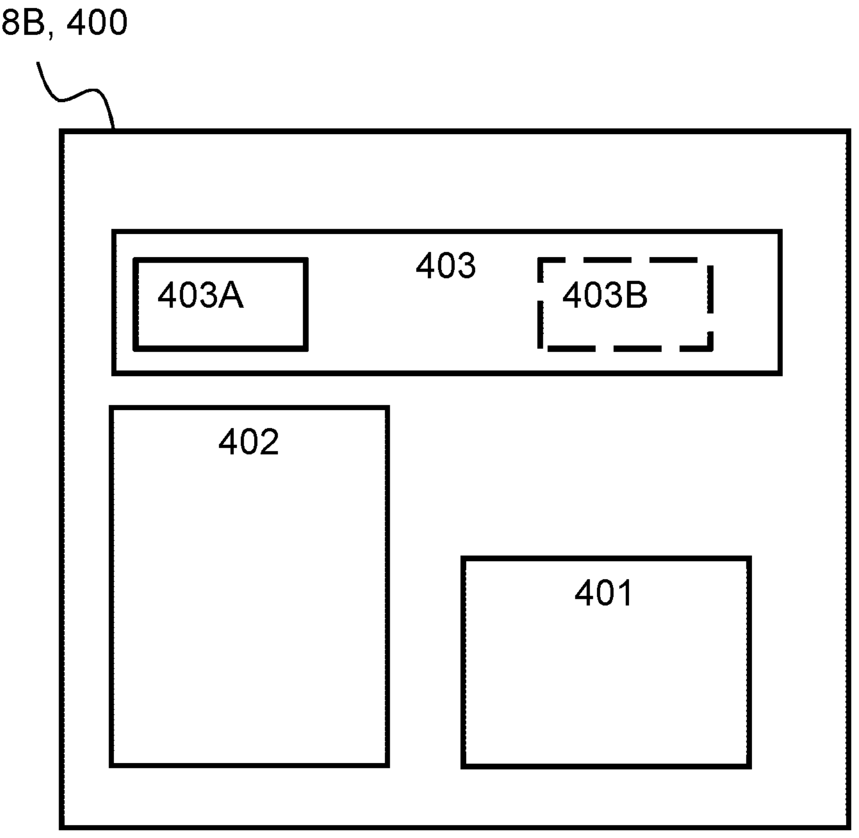
FIG. 4 is a block diagram illustrating an exemplary secondary accessory device according to the present disclosure.

FIG. 4 is a block diagram illustrating an exemplary secondary accessory device 400, 8B according to the present disclosure. The secondary accessory device 400 forms part of a personal care system, such as an ostomy system or a wound dressing system and is capable of supporting the monitoring of the operating state of an ostomy appliance or a wound dressing appliance to be placed on a user's skin. The secondary accessory device 400 comprises a memory 401; a processor 402 coupled to the memory 401; and an interface 403, coupled to the processor 402.

Peripheral devices, such as memory 401 and/or interface 403 can be operatively and communicably coupled to the processor 402 via a bus for communicating data. The processor 402 can be a central processing unit (CPU), but other suitable microprocessors are also contemplated.

The interface 403 is configured to connect the secondary accessory device to the monitor device of the personal care system, the interface comprising a transceiver module 403A connected to the processor 402.

The interface 403 may be configured to communicate with one or more devices of the personal care system. The one or more devices comprising a monitor device, optionally a primary accessory device and/or a personal care appliance configured to be placed on a skin surface of a user or on any additional seals. The interface 403 may comprise a display 403B as a visual interface to the user. The interface 403 is configured to establish a secondary connection between the monitor device and the secondary accessory device.

The interface 403 is configured to receive secondary monitor data from the monitor device, such as to receive or retrieve the secondary monitor data from the one or more devices. The secondary monitor data may be indicative of a primary connection between the monitor device and the primary accessory device and/or indicative of a condition of the personal care appliance, such as a condition of a proximal side of a layer of the personal care appliance that is directed towards the skin surface or a condition of an absorbent core layer of the personal care appliance. In one or more exemplary secondary accessory devices, the secondary monitor data comprises appliance data, e.g. ostomy data or wound dressing data, obtained via the interface 403 from an ostomy appliance being the personal care appliance or from a wound dressing being the personal care appliance, respectively.

The processor 402 is configured to determine and/or communicate a secondary indication based on the secondary monitor data. The secondary monitor data may be indicative of a primary connection between the monitor device and the primary accessory device being lost or degraded.

The secondary accessory device/processor 402 is optionally configured to select, from a plurality of indications, the secondary indication indicative of the quality of the primary connection. In one or more exemplary secondary accessory devices, the secondary indication is indicative of the operating state at a time where the monitor device and/or the primary accessory device determines that a first primary criterion based on the quality of the primary connection is not satisfied. For example, the secondary indication may be indicative of the operating state at a time where the primary connection is lost and/or degraded and/or interrupted. The secondary accessory device is optionally configured to, e.g. in accordance with receiving secondary monitor data indicative of the primary connection being lost or degraded, determine, such as select, obtain, and/or generate, the secondary indication indicative of the quality of the primary connection. For example, the secondary indication may be indicative of the operating state of the personal care appliance at a time where the primary connection is lost and/or degraded and/or interrupted.

The processor 402 may be configured to determine an operating state of the personal care appliance based on the secondary monitor data.

The accessory device 400 is capable of communicating a secondary indication indicative of a quality of the primary connection. The present disclosure improves the reliability of the monitoring performed by the personal care system, by communicating the secondary indication indicative of the quality of primary connection when a quality of the primary connection is not satisfactory, e.g. as indicated by the secondary monitor data. The secondary accessory device 400 can notify appropriately the user and to start potentially determining or estimating the operating state based on the secondary monitor data. For example, communication of the secondary indication indicative of a quality of the primary connection to the monitor device helps reducing the risk of a user experiencing a leakage (e.g. output leakage between a user's skin and the baseplate of the ostomy appliance) from an ostomy appliance in a planned activity and/or wet wound from a saturated wound dressing appliance. In particular, determination and communication the secondary indication indicative of an estimated operating state, and possibly with a latest operating state, according to the present disclosure is performed based on secondary monitor data indicative of a condition of the personal care appliance which may not be visible to the user.

The secondary accessory device is configured to, e.g. based on the secondary monitor data and/or primary accessory data, communicate the secondary indication, e.g. to the user, e.g. via an output device (such as a display and/or a loudspeaker) of the secondary accessory device. In one or more exemplary embodiments, the secondary indication may be communicated by sound.

The secondary accessory device 400 is optionally configured to establish an accessory connection between the primary accessory device and the secondary accessory device; receive primary accessory data from the primary accessory device; and determine the secondary indication based on the primary accessory data.

The processor 402 is optionally configured to, in accordance with a determination that the quality of primary connection is not satisfactory, select, from a plurality of indications, the secondary indication indicative of the quality of the primary connection. In one or more exemplary accessory devices, the second indication is indicative of the operating state at a time where the quality of the primary connection is not satisfactory. For example, the secondary indication may be indicative of the operating state at a time where the primary connection is lost and/or degraded and/or interrupted. For example, the secondary indication may be selected from the plurality of indications comprising an indication indicative of the primary connection lost and/or degraded, and an indication indicative of the operating state at a time where the quality of the primary connection is not satisfactory.

To select the secondary indication indicative of the quality of the primary connection may comprise to determine an estimated operating state of the personal care appliance based on one or more previous operating states of the personal care appliance. For example, the processor 402 determines the estimated operating state of the personal care appliance based on one or more previous operating states and selects the secondary indication amongst a plurality of indications including an indication indicative of the estimated operating state. The one or more previous operating states of the personal care appliance are determined by the secondary accessory device before the time where the quality of the connection is not satisfactory (e.g. before the time where the primary connection is lost). In one or more exemplary secondary accessory devices, the secondary indication is indicative of the estimated operating state.

In one or more exemplary secondary accessory devices, the processor 402 is configured to, in accordance with a determination that the quality of the primary connection is not satisfactory, e.g. the primary connection is lost, communicate, e.g. via the interface 403, the secondary indication indicative of the quality of the primary connection, by displaying, on a display 403B, a first user interface object representative of the secondary indication. The first user interface object may be displayed as one or more media, such as text, graphic and/or video. The interface 403 may comprise the display 403B configured to display a user interface. The display 403B may comprise a touch sensitive surface. A user interface comprises one or more user interface objects. A user interface may be referred to as a user interface screen.

The display 403B may be configured to detect touch (e.g. the display is a touch-sensitive display), the input comprises a contact on the touch sensitive display. A touch-sensitive display provides an input interface and an output interface between the accessory device and a user. The processor 402 of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user interface objects.

In one or more exemplary secondary accessory devices, to communicate the secondary indication comprises to display, on a visual interface (e.g. a display 403B) of the accessory device, a user interface comprising a user interface object representative of the secondary indication, such as a first user interface object representative of the secondary indication indicative of the quality of the primary connection and/or representative of a first operating state of the personal care appliance, and/or representative of a second operating state of the personal care appliance. In one or more exemplary accessory devices, the user interface object representative of the secondary indication comprises a first user interface object representative of the secondary indication, and/or of one or more operating states.

In one or more exemplary secondary accessory devices, to communicate the secondary indication comprises to notify the user via the interface, such as by displaying a notification on a display of the secondary accessory device 400. The notification may comprise the first user interface object representative of the secondary indication. The notification may comprise a notification indicator to open an application related to the personal care appliance. The secondary accessory device 400 may be configured to detect an input on the notification indicator. The secondary accessory device 400 may be configured to, in response to the input, opening the application related to the personal care appliance. The secondary accessory device 400 may be configured to, in response to the opening of the application, to display a user interface object representative of an operating state (such as a latest operating state and/or an estimated operating state). For example, the first user interface object may convey: "Connection to primary accessory device lost" and/or "everything is good".

The secondary accessory device 400 may be configured to determine whether the primary connection has been resumed/re-established, e.g. based on the secondary monitor data from the monitor device and/or primary accessory data from the primary accessory device.

The secondary accessory device 400 may be configured to, in accordance with a determination that the primary connection is resumed or has increased quality, communicate a tertiary indication indicative of the quality of the primary connection. The secondary accessory device 400 may be configured to in accordance with a determination that the primary connection has been resumed, determine the tertiary indication.

The secondary accessory device 400 is optionally configured to, in accordance with a determination that the primary connection is resumed or has increased quality, determine, such as select, obtain, and/or generate, the tertiary indication indicative of the quality of the primary connection. For example, the tertiary indication may be indicative of an operating state based on secondary monitor data received from the monitor device at the time that the primary connection has been resumed, such as based on secondary monitor data stored in the monitor device.

The tertiary indication is optionally indicative of the operating state at a time where the primary connection is resumed or has increased quality. For example, the tertiary indication may be indicative of the operating state at a time where the primary connection is resumed, such as re-established.

The secondary monitor data may comprise ostomy data obtained from an ostomy appliance being the personal care appliance via the interface or wound dressing data obtained from a wound dressing being the personal care appliance via the interface.

The secondary accessory device 400 may be configured to, in accordance with a determination that the primary connection is resumed or has increased quality, communicate the tertiary indication indicative of the quality of the primary connection, by displaying, on the display of the accessory device, a second user interface object representative of the tertiary indication. For example, the second user interface object may convey: "Connection to primary accessory device resumed" and/or "everything is still good". For example, to communicate the tertiary indication may comprise to notify the user via the interface, such as by displaying a notification indicative of the tertiary indication on a display of the secondary accessory device.

The memory 401 may be configured to store the secondary monitor data and/or the operating state and/or the secondary indication(s) and/or tertiary indication(s).

Figure 5A:
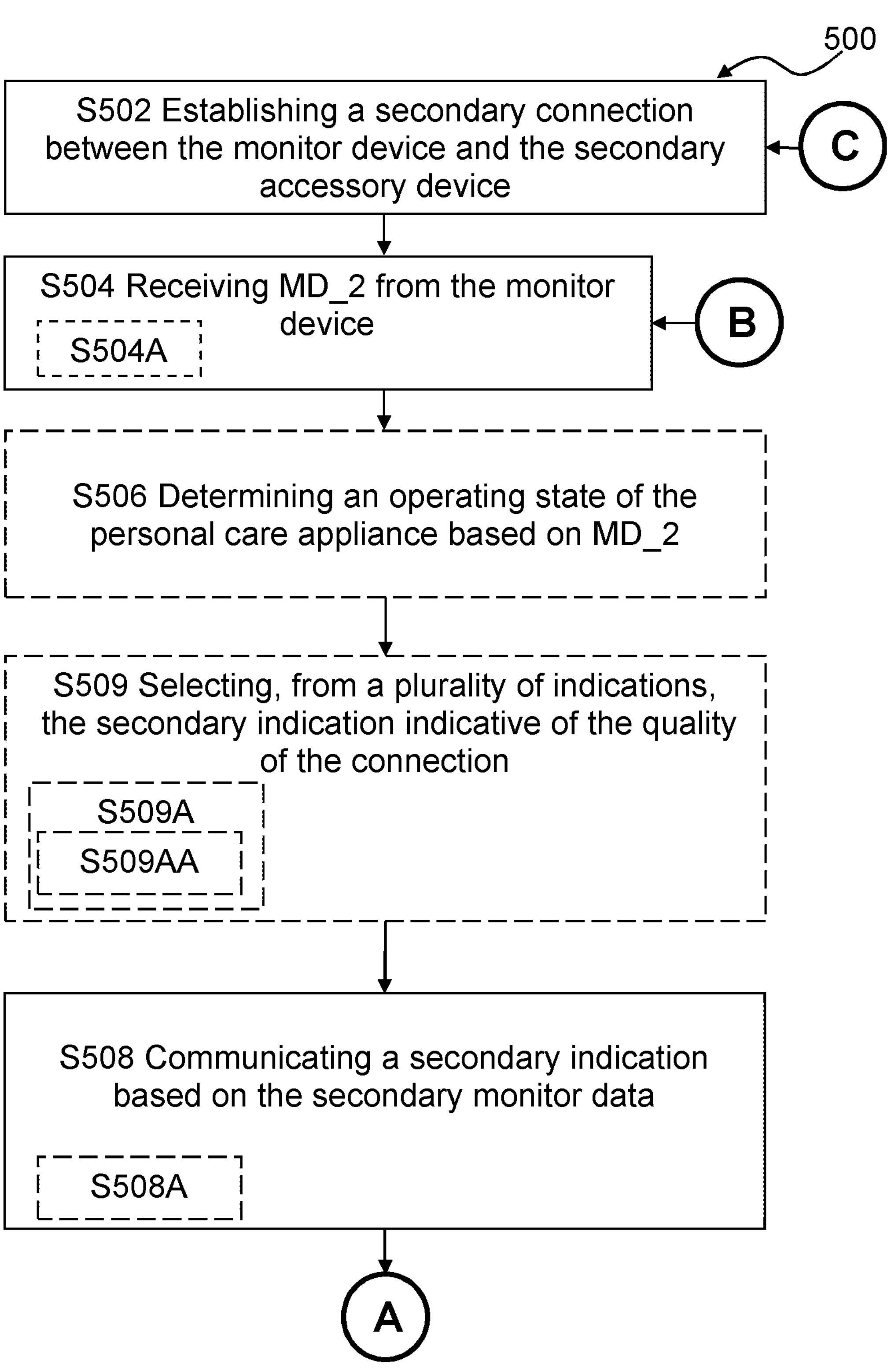
FIGS. 5A and 5B show a flow diagram of an example method of operating a secondary accessory device for a personal care system according to the present disclosure.
Figure 5B:
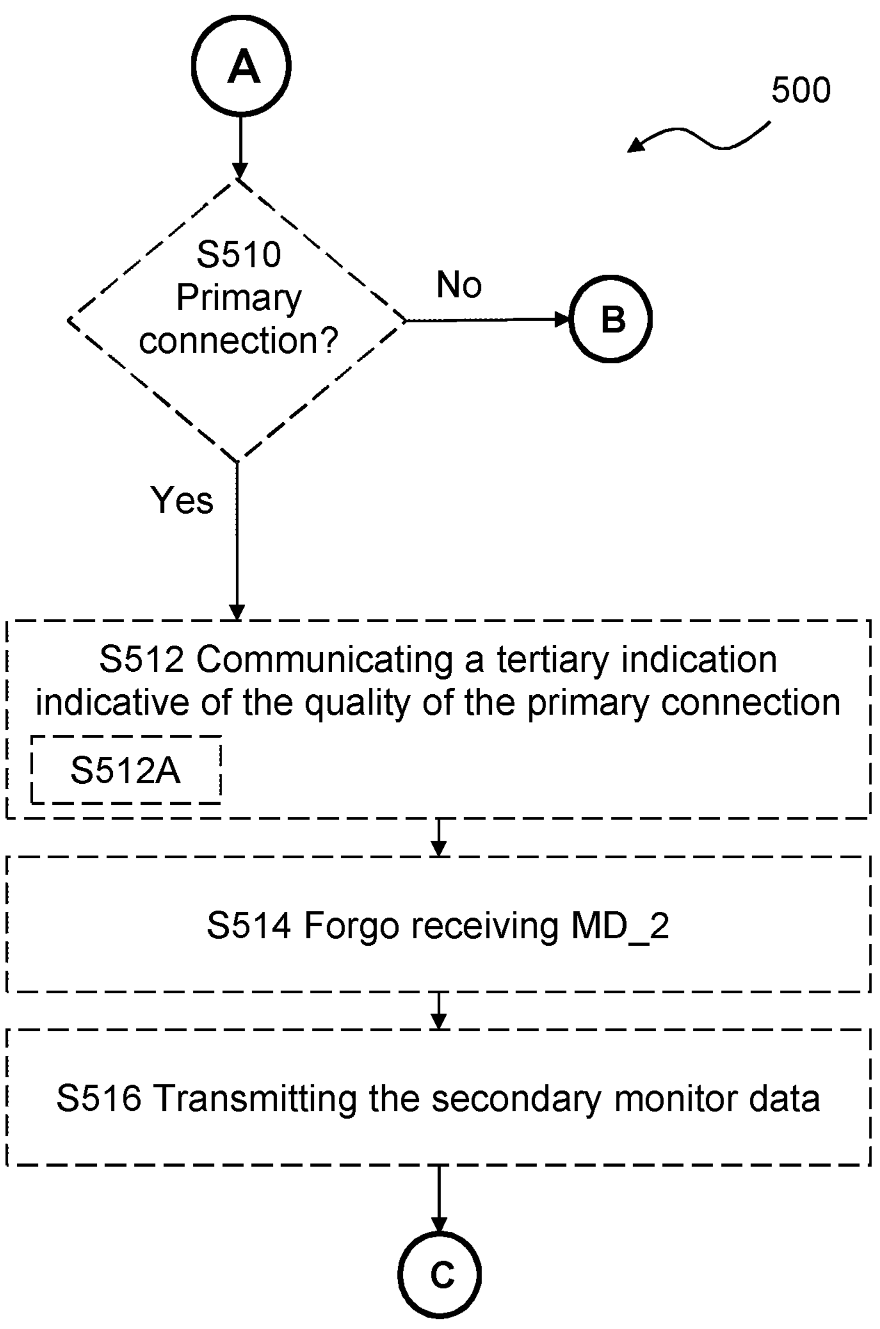

The processor 402 is optionally configured to perform any of the operations disclosed in FIGS. 5A and 5B.

The processor 402 may be optionally configured to perform any of the operations disclosed in FIG. 5 (such as any one or more of S506, S508, S509, S509A, 509AA, S510, S512, S512A, S514, S516). The operations of the secondary accessory device 400 may be embodied in the form of executable logic routines (such as, lines of code, software programs, etc.) that are stored on a non-transitory computer readable medium (such as, the memory 401) and are executed by the processor 402).

Furthermore, the operations of the secondary accessory device 400 may be considered a method that the secondary accessory device 400 is configured to carry out. Also, while the described functions and operations may be implemented in software, such functionality may as well be carried out via dedicated hardware or firmware, or some combination of hardware, firmware and/or software.

The memory 401 may be one or more of a buffer, a flash memory, a hard drive, a removable media, a volatile memory, a non-volatile memory, a random access memory (RAM), or other suitable device. In a typical arrangement, the memory 401 may include a non-volatile memory for long term data storage and a volatile memory that functions as system memory for the processor 402. The memory 401 may exchange data with the processor 402 over a data bus. Control lines and an address bus between the memory 401 and the processor 402 also may be present (not shown in FIG. 4). The memory 401 is considered a non-transitory computer readable medium.

FIGS. 5A and 5B shows a flow diagram of an example method 500 of operating a secondary accessory device for a personal care system. The personal care system comprises a personal care appliance, a monitor device, a primary accessory device, and the secondary accessory device.

The method 500 of operating a secondary accessory device for a personal care system comprises establishing S502 a secondary connection between the monitor device and the secondary accessory device, receiving S504 secondary monitor data from the monitor device. Receiving S504 secondary monitor data from the monitor device optionally comprises storing S504A the secondary monitor data in the memory. The method optionally comprises determining S506 an operating state of the personal care appliance based on the secondary monitor data MD_2. The method 500 comprises communicating S508 a secondary indication based on the secondary monitor data and optionally indicative of the quality of the primary connection, such as indicative of a first primary connection criterion not being satisfied in the monitor device and/or in the primary accessory device.

The method 500 optionally comprises selecting S509, from a plurality of indications, the secondary indication indicative of the quality of the primary connection.

In the method 500, communicating S508 the secondary indication indicative of the quality of the primary connection comprises displaying S508A, on a display of the secondary accessory device, a first user interface object representative of the secondary indication.

In the method 500, selecting S509 the secondary indication indicative of the quality of the primary connection optionally comprises determining S509A an estimated operating state of the personal care appliance based on one or more previous operating states of the personal care appliance. Determining S509A the estimated operating state of the personal care appliance based on the one or more previous operating states of the personal care appliance may comprise predicting S509AA the estimated operating state of the personal care appliance based on the one or more previous operating states of the personal care appliance. The secondary indication may be indicative of the operating state at a time where the primary connection is lost or degraded. The secondary indication is optionally indicative of the estimated operating state.

The method 500 may comprise determining S510 whether the primary connection has been resumed or re-established, e.g. based on the secondary monitor data and/primary accessory data. The method 500 optionally comprises, in accordance with a determination that the primary connection has been resumed or re-established, communicating S512 a tertiary indication indicative of the quality of the primary connection. The tertiary indication may be indicative of the operating state at a time where the primary connection has been resumed or re-established. For example, the tertiary indication is optionally indicative of the operating state at a time where the primary connection is resumed, such as re-established. Communicating S512 the tertiary indication indicative of the quality of the connection optionally comprises displaying S512A, on the display of the accessory device, a second user interface object representative of the tertiary indication. The method 500 optionally comprises, in accordance with a determination that the primary connection has been resumed or re-established, forgo S514 receiving the secondary monitor data and/or transmitting S516 secondary monitor data stored in memory of the secondary accessory device to the primary accessory device.

Figure 6:
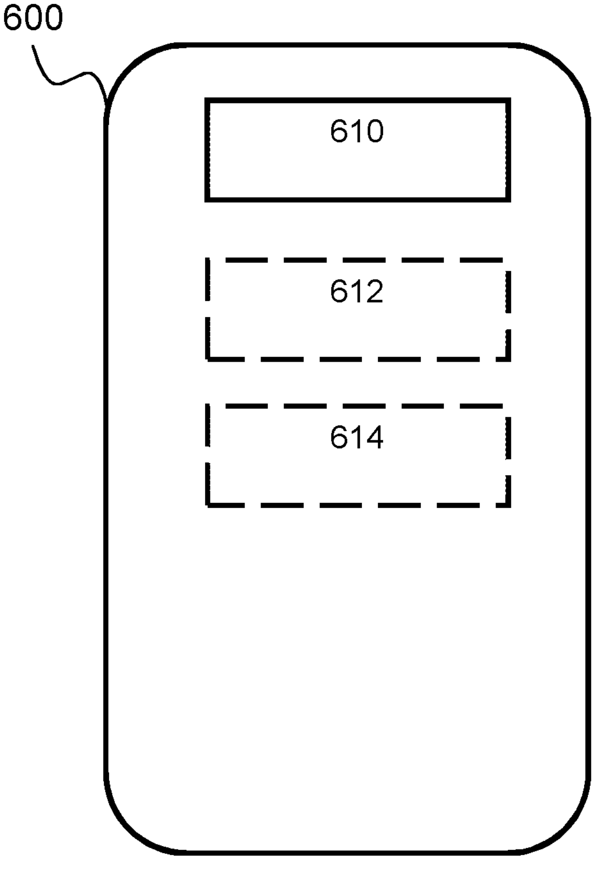
FIG. 6 shows one or more exemplary user interfaces for communicating the secondary indication according to the present disclosure.

FIG. 6 illustrates one or more exemplary user interfaces for communicating the secondary indication according to the present disclosure. FIG. 6 shows an exemplary user interface 600 for communicating the secondary indication via a visual interface of the accessory device, such as a display of the secondary accessory device.

The user interface 600 comprises a first user interface object 610 representative of the secondary indication indicative of the quality of primary connection between the monitor device and the primary accessory device. The first user interface object 610 may be displayed as one or more media, such as text, graphic and/or video. The first user interface object 610 may comprise the text "Connection to primary device lost".

The first user interface object 610 may be user-interactive, or selectable by a user input. For example, an image (e.g., icon), a button, and text (e.g., hyperlink) each optionally constitute the first user interface object 610. The first user interface object 610 may form part of a widget.

The user interface 600 may comprise one or more, such as a plurality of user interface objects. For example, the user interface may comprise a first primary user interface object 612 representative of the secondary indication indicative of an operating state at the time of primary connection loss. For example, the user interface may comprise a first secondary user interface object 614 representative of the secondary indication indicative of an estimated operating state.

The accessory device is optionally configured to change dynamically the visual appearance of any of the user interface objects 610, 612, 614 based on the operating state. e.g. in terms of text, colour, shape, form, contrast, brightness, animation and/or blurring to indicate the operating state (latest or estimated for current time). For example, the severity of the operating state may be displayed, by the secondary accessory device, by varying in colour: e.g. blue, yellow, red for indicating low, medium, high severity respectively. For example, the severity of the operating state of the personal care appliance may be displayed, by the accessory device, by varying shades within a colour from a lighter shade to a darker shade for indicating low to high severity respectively. For example, the severity of the operating state may be displayed, by the secondary accessory device, by varying a magnitude of the visual effect (e.g., less blurring, sharper contrast) as severity increases.

For example, the user interface object 610 and/or 612, and/or 614 may be representative of an operating state indicating to change NOW the personal care by adopting e.g. the colour red, in a dark shade, in sharp contrast.

In one or more exemplary user interfaces, the user interface 600 comprises user interface objects 610, 612, 614 which separately or together, display a text prompt indicating to the user the secondary indication. A text prompt may for example indicate: "Primary connection lost—Everything is fine", "Primary connection lost—Good", "Primary connection lost—Check", "Primary connection lost—Change".

For example, the user interface object 610 and/or 612, and/or 614 may be displayed as one or more notifications, such as in a notification centre displayed on the display.

The secondary accessory device may be configured to provide the user interface 600 in a user application running on the processor. The user application may be a dedicated personal care application that assist the user in monitoring the internal operating state of the personal care appliance.

The secondary accessory device may be configured to provide the user interface 600 on a lock screen displayed by the secondary accessory device.

The secondary accessory device may be configured to provide the user interface 600 on a home screen displayed by the secondary accessory device.

Figure 7:
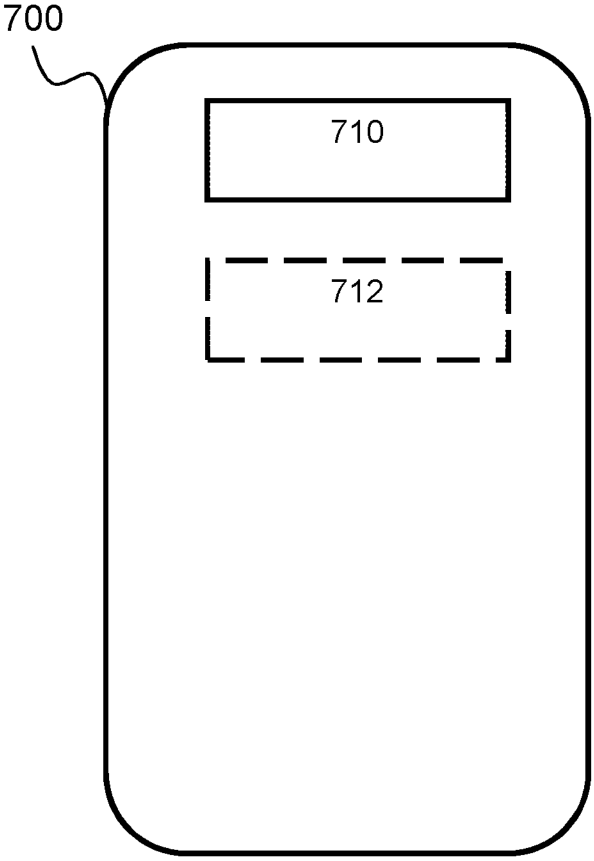
FIG. 7 shows one or more exemplary user interfaces for communicating the tertiary indication according to the present disclosure.

FIG. 7 shows an exemplary user interface 700 for communicating the tertiary indication via a visual interface of the accessory device, such as a display of the secondary accessory device.

The user interface 700 comprises a second user interface object 710 representative of the tertiary indication indicative of the quality of primary connection between the monitor device and the primary accessory device. The second user interface object 710 may be displayed as one or more media, such as text, graphic and/or video.

The second user interface object 710 may be user-interactive, or selectable by a user input. For example, an image (e.g., icon), a button, and text (e.g., hyperlink) each optionally constitute the second user interface object 710. The second user interface object 710 may form part of a widget.

The user interface 700 may comprise one or more, such as a plurality of user interface objects. For example, the user interface may comprise a second primary user interface object 712 representative of the second indication indicative of an operating state at the time of connection resumed (at a time where the second primary connection criterion based on a quality of the primary connection is satisfied).

The secondary accessory device is optionally configured to change dynamically the visual appearance of any of the user interface object 712 based on the operating state of the personal care appliance, e.g. in terms of colour, shape, form, contrast, brightness, animation and/or blurring to indicate the operating state (latest or estimated for current time). For example, the severity of the operating state may be displayed, by the secondary accessory device, by varying in colour: e.g. blue, yellow, red for indicating low, medium, high severity respectively. For example, the severity of the operating state may be displayed, by the secondary accessory device, by varying shades within a colour from a lighter shade to a darker shade for indicating low to high severity respectively. For example, the severity of the operating state may be displayed, by the secondary accessory device, by varying a magnitude of the visual effect (e.g., less blurring, sharper contrast) as severity increases.

For example, the user interface object 710 and/or 712, may be representative of an operating state indicating to change NOW the personal care by adopting e.g. the colour red, in a dark shade, in sharp contrast.

In one or more exemplary user interfaces, the user interface 700 comprises user interface objects 710, 712 which separately or together, display a text prompt indicating to the user the tertiary indication. A text prompt may for example indicate: "Primary connection resumed—Everything is fine", "Primary connection resumed—Good", "Primary connection resumed—Check", "Primary connection resumed—Change".

For example, the user interface object 710 and/or 712, may be displayed as one or more notifications, such as in a notification centre displayed on the display.

The accessory device may be configured to provide the user interface 700 in the user application running on the processor dedicated to personal care.

The accessory device may be configured to provide the user interface 700 on a lock screen displayed by the secondary accessory device.

The secondary accessory device may be configured to provide the user interface 600 on a home screen or a clock face displayed by the secondary accessory device.

FIG. 8 illustrates an exemplary personal care system 1 embodied as a wound dressing system 1B. The personal care system 1 (wound dressing system 1B) comprises a personal care appliance 2 embodied as a wound dressing appliance 2B.

Figure 9:
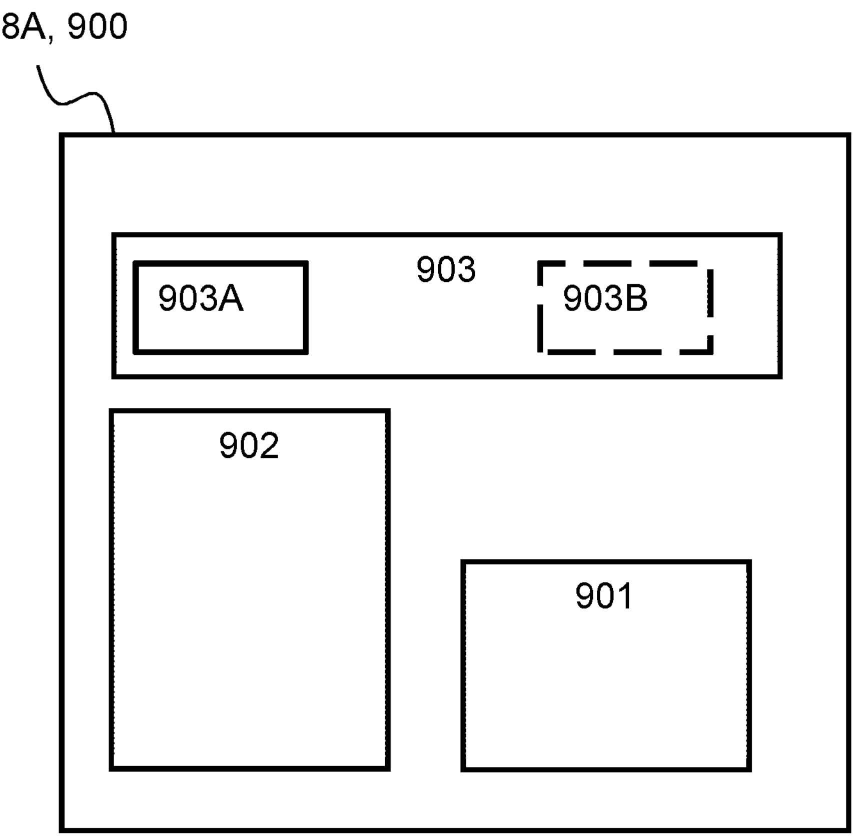
FIG. 9 is a block diagram illustrating an exemplary primary accessory device according to the present disclosure.

FIG. 9 is a block diagram illustrating an exemplary primary accessory device 900, 8A according to the present disclosure. The primary accessory device 900 forms part of a personal care system, such as an ostomy system or a wound dressing system and is capable of supporting the monitoring of the operating state of an ostomy appliance or a wound dressing appliance to be placed on a user's skin. The primary accessory device 900 comprises a memory 901; a processor 902 coupled to the memory 901; and an interface 903, coupled to the processor 902.

Peripheral devices, such as memory 901 and/or interface 903 can be operatively and communicably coupled to the processor 902 via a bus for communicating data. The processor 902 can be a central processing unit (CPU), but other suitable microprocessors are also contemplated.

The interface 903 is configured to connect the secondary accessory device to the monitor device of the personal care system, the interface comprising a transceiver module 903A connected to the processor 902.

The interface 903 may be configured to communicate with one or more devices of the personal care system. The one or more devices comprising a monitor device, optionally a secondary accessory device and/or a personal care appliance configured to be placed on a skin surface of a user or on any additional seals. The interface 903 may comprise a display 903B as a visual interface to the user. The interface 903 is configured to establish a primary connection between the monitor device and the primary accessory device.

The interface 903 is configured to receive primary monitor data from the monitor device, such as to receive or retrieve the primary monitor data from the one or more devices.

The interface 903 is configured to establish an accessory connection between the primary accessory device and the secondary accessory device.

The primary accessory device 900/processor 902 is configured to, determine whether a first primary connection criterion based on a quality of the primary connection is satisfied; and in accordance with a determination that the first primary connection criterion is not satisfied receive secondary accessory data from the secondary accessory device; and/or communicate a primary indication to the secondary accessory device, e.g. by transmitting primary accessory data to the secondary accessory device. The primary accessory data may comprise previously received primary monitor data and/or previously determined operating states of the personal care appliance, such as base plate. The primary indication may be indicative of loss of primary connection. The secondary accessory data may comprise secondary monitor data and/or operating states of the personal care appliance, such as base plate, determined by the secondary accessory device.

The primary accessory device 900 is optionally configured to, in accordance with a determination that the first primary connection criterion is not satisfied, transmit primary accessory data to the secondary accessory device. Thereby the primary accessory device may be configured to inform the secondary accessory device on historical monitor data and/or current or previous operating states of the personal care appliance, in turn enabling the secondary accessory device more precise operating state determinations and/or secondary indications.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-9 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented.

Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

1 personal care system
1A ostomy system
1B wound dressing system
2 personal care appliance
2A ostomy appliance
2B wound dressing appliance
4 base plate
6 monitor device
8A primary accessory device, smartphone

8B secondary accessory device, smartwatch
9A primary connection between the monitor device and the primary accessory device
9B secondary connection between the monitor device and the secondary accessory device
9C accessory connection between the primary accessory device and the secondary accessory device
10 server device
12 network
14 coupling member
16 coupling ring
18 stoma-receiving opening
19 center of the opening
20 docking station
22 first connector
24 user interface
100 monitor device housing
101 processor
102 first interface
104 second interface
106, 106A memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver, transceiver module
126 loudspeaker
128 haptic feedback element
140 sensor unit
142, MD_1 primary monitor data
144, MD_2 secondary monitor data
300 method of operating a monitor device for a personal care system
S302 establishing a primary connection between the monitor device and the primary accessory device
S304 transmitting primary monitor data to the primary accessory device via the primary connection
S308 determining whether a first primary connection criterion based on a quality of the primary connection is satisfied
S310 transmitting secondary monitor data to the secondary accessory device
S311 establishing a secondary connection between the monitor device and the secondary accessory device
S312 determining the secondary monitor data
S313 forgo transmitting primary monitor data
S314 determining whether a second primary connection criterion is satisfied
S316 notifying the secondary accessory device
S318 forgo transmitting the secondary monitor data
400 secondary accessory device
401 memory of accessory device
402 processor of accessory device
403 interface of accessory device
403 transceiver
403B display
500 Method of operating a secondary accessory device
S502 establishing a secondary connection between the monitor device and the secondary accessory device
S504 receiving secondary monitor data from the monitor device
S504A storing secondary monitor data in memory
S506 determining an operating state of the personal care appliance based on the secondary monitor data
S508 communicating a secondary indication indicative of the quality of the primary connection
S509 selecting, from a plurality of indications, the secondary indication indicative of the quality of the connection
S509A determining the estimated operating state of the personal care appliance based on the one or more previous operating states of the personal care appliance
S509AA predicting the estimated operating state of the personal care appliance based on the one or more previous operating states of the personal care appliance
S510 determining whether a quality of the primary connection is satisfactory
S512 communicating a tertiary indication indicative of the quality of the primary connection
S512A displaying, on the display of the secondary accessory device, a second user interface object representative of the second indication
S514 forgo receiving secondary monitor data
S516 transmitting the secondary monitor data stored in the memory
600 user interface
610 first user interface object
612 first primary user interface object
614 first secondary user interface object
700 user interface
710 second user interface object
712 second primary user interface object
900 secondary accessory device
901 memory of accessory device
902 processor of accessory device
903 interface of accessory device
903 transceiver
903B display

The invention claimed is:

1. A personal care system comprising:

a personal care appliance, a primary accessory device being a handheld device, a secondary accessory device being a handheld device, and a monitor device, the monitor device comprising:

a processor;

a memory connected to the processor, the memory including instructions that are executable by the processor;

a first interface connected to the processor, the first interface configured for connecting the monitor device to the personal care appliance; and a second interface comprising a transceiver module connected to the processor and configured for connecting the monitor device to the primary accessory device and the secondary accessory device, wherein the instructions, when executed by the at least one processor, cause the monitor device to perform a set of operations, the set of operations including:

establishing a primary connection between the monitor device and the primary accessory device;

transmitting primary monitor data to the primary accessory device via the primary connection;

determining whether a first primary connection criterion based on a quality of the primary connection is satisfied; and in accordance with a determination that the first primary connection criterion is not satisfied, transmitting secondary monitor data to the secondary accessory device.

2. The personal care system according to claim 1, wherein the first primary connection criterion based on a quality of the primary connection is not satisfied when it is determined that the quality of the primary connection is not above a first primary connection threshold.

3. The personal care system according to claim 1, wherein the set of operations further includes, in accordance with the determination that the first primary connection criterion is not satisfied, forgo transmitting primary monitor data to the primary accessory device.

4. The personal care system according claim 1, wherein the set of operations further includes, in accordance with the determination that the first primary connection criterion is not satisfied, establishing a secondary connection to the secondary accessory device, wherein the secondary monitor data is transmitted via the secondary connection.

5. The personal care system according to claim 1, wherein the set of operations further includes, in accordance with the determination that the first primary connection criterion is not satisfied, determining the secondary monitor data.

6. The personal care system according to claim 5, wherein determining the secondary monitor data is based on a type of the secondary accessory device.

7. The personal care system according to claim 6, wherein determining the secondary monitor data comprises selecting first secondary monitor data as the secondary monitor data in accordance with the secondary accessory device being a first type and selecting second secondary monitor data as the secondary monitor data in accordance with the secondary accessory device being a second type.

8. The personal care system according to claim 5, wherein determining the secondary monitor data is based on an operating state of the personal care appliance.

9. The personal care system according to claim 1, wherein the set of operations further includes:

determining whether a second primary connection criterion based on a quality of the primary connection is satisfied; and in accordance with a determination that the second primary connection criterion is satisfied, resume to transmitting primary monitor data to the primary accessory device.

10. The personal care system according to claim 9, wherein the second primary connection criterion based on a quality of the primary connection is satisfied when it is determined that the quality of the primary connection is above a second primary connection threshold or when it is determined that the primary connection is resumed.

11. The personal care system according to claim 9, wherein the set of operations further includes, in accordance with the determination that the second primary connection criterion is satisfied, forgo to transmitting secondary monitor data to the secondary accessory device.

12. The personal care system according to claim 1, wherein the primary monitor data comprises primary ostomy data obtained from an ostomy appliance being the personal care appliance via the first interface or primary wound dressing data obtained from a wound dressing being the personal care appliance via the first interface.

13. The personal care system according to claim 1, the personal care appliance being an ostomy appliance or a wound dressing.

14. A method of operating a monitor device for a personal care system comprising a personal care appliance, the monitor device, a primary accessory device, and a secondary accessory device, wherein the primary accessory device is a first handheld device and the secondary accessory device is a second handheld device, the method comprising:

establishing a primary connection between the monitor device and the primary accessory device;

establishing a secondary connection between the monitor device and the second accessory device, wherein the secondary connection is independent of the primary connection, and wherein a secondary monitor data is transmitted via the secondary connection;

transmitting primary monitor data to the primary accessory device via the primary connection;

determining that a first primary connection criterion based on if a quality of the primary connection is satisfied; and in accordance with a determination that the first primary connection criterion is not satisfied, transmitting the secondary monitor data to the secondary accessory device via the secondary connection.

15. The method according to claim 14, wherein the first primary connection criterion is not satisfied when determining that the quality of the primary connection is not above a first primary connection threshold.

16. The method according to claim 14, wherein the method comprises, in accordance with the determination that the first primary connection criterion is not satisfied, to forgo transmitting primary monitor data to the primary accessory device.

17. The method according to claim 14, wherein the method comprises, in accordance with the determination that the first primary connection criterion is not satisfied, determining the secondary monitor data.

18. The method according to claim 17, wherein determining the secondary monitor data is based on a type of the secondary accessory device.

19. The method according to claim 18, wherein determining the secondary monitor data comprises selecting first secondary monitor data as the secondary monitor data in accordance with the secondary accessory device being a first type and selecting second secondary monitor data as the secondary monitor data in accordance with the secondary accessory device being a second type.

20. The method according to claim 17, wherein determining the secondary monitor data is based on an operating state of the personal care appliance.

21. The method according to claim 14, wherein the method comprises:

determining whether a second primary connection criterion based on a quality of the primary connection is satisfied; and in accordance with a determination that the second primary connection criterion is satisfied, to resume transmitting primary monitor data to the primary accessory device.

22. The method according to claim 21, wherein the second primary connection criterion based on a quality of the primary connection is satisfied when it is determined that the quality of the primary connection is above a second primary connection threshold or when it is determined that the primary connection is resumed.

23. The method according to claim 21, wherein the method comprises, in accordance with a determination that the second primary connection criterion is satisfied, to forgo transmitting secondary monitor data to the secondary accessory device.

24. The method according to claim 14, wherein the personal care appliance is an ostomy appliance, and the method comprises obtaining ostomy data from the ostomy appliance and including the ostomy data in the primary monitor data; or wherein the personal care appliance is a wound dressing, and the method comprises obtaining wound dressing data from the wound dressing and including the primary wound dressing data in the primary monitor data.

25. The personal care system according to claim 1, wherein the primary accessory device is one of a smartphone, a tablet, or a smartwatch, and wherein the secondary accessory device is one of a smartphone, a tablet, or a smartwatch.

26. The personal care system according to claim 1, wherein the primary accessory device is configured to establish an accessory connection with the secondary device.

27. The method of claim 14, wherein the secondary monitor data includes less information than the primary monitor data.

28. The method of claim 14, wherein the secondary monitor data is substantially the same as the primary monitor data.

29. The method according to claim 14, wherein the primary accessory device is one of a smartphone, a tablet, or a smartwatch.

30. The method according to claim 14, wherein the secondary accessory device is one of a smartphone, a tablet, or a smartwatch.

31. The method of claim 1, further including establishing a secondary connection between the monitor device and the second accessory device, wherein the secondary connection is independent of the primary connection, and wherein the secondary monitor data is transmitted via the secondary connection.

32. The method of claim 1, wherein the primary accessory device, the second accessory device, and the monitor device are separate, independent devices.

33. The method of claim 14, wherein the primary accessory device, the second accessory device, and the monitor device are separate, independent devices.

34. The method of claim 14, performed by the monitor device including at least one processor and a memory connected to the processor, the memory including instructions that are executable by the processor to cause the monitor device to perform the method.

35. The method of claim 24, wherein the monitor device is positioned on a base plate of the personal care appliance.

* * * * *